(12) United States Patent
Kalmeta

(10) Patent No.: US 11,684,797 B2
(45) Date of Patent: *Jun. 27, 2023

(54) LASER ASSISTED WOUND HEALING PROTOCOL AND SYSTEM

(71) Applicant: BIOREGENTECH, INC., Irvine, CA (US)

(72) Inventor: Margaret Kalmeta, Irvine, CA (US)

(73) Assignee: THE BIOREGENTECH INSTITUTE, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/735,034

(22) Filed: May 2, 2022

(65) Prior Publication Data

US 2022/0257970 A1 Aug. 18, 2022

Related U.S. Application Data

(63) Continuation of application No. 15/348,793, filed on Nov. 10, 2016, now Pat. No. 11,389,663, which is a (Continued)

(51) Int. Cl.

| | |
|---|---|
| *A61K 33/42* | (2006.01) |
| *A61K 38/39* | (2006.01) |
| *A61K 33/00* | (2006.01) |
| *A61K 33/38* | (2006.01) |
| *A61K 33/34* | (2006.01) |
| *A61K 33/24* | (2019.01) |
| *A61K 33/26* | (2006.01) |
| *A61K 8/41* | (2006.01) |
| *A61K 31/07* | (2006.01) |
| *A61K 8/24* | (2006.01) |
| *A61K 8/44* | (2006.01) |
| *A61K 8/20* | (2006.01) |
| *A61Q 11/00* | (2006.01) |
| *A61K 31/714* | (2006.01) |
| *A61K 31/7004* | (2006.01) |
| *A61K 31/122* | (2006.01) |
| *A61K 33/14* | (2006.01) |
| *A61N 5/06* | (2006.01) |
| *A61N 1/40* | (2006.01) |

(Continued)

(52) U.S. Cl.
CPC .......... *A61N 5/0603* (2013.01); *A61C 1/0046* (2013.01); *A61K 8/20* (2013.01); *A61K 8/24* (2013.01); *A61K 8/368* (2013.01); *A61K 8/416* (2013.01); *A61K 8/44* (2013.01); *A61K 8/442* (2013.01); *A61K 8/65* (2013.01); *A61K 31/07* (2013.01); *A61K 31/122* (2013.01); *A61K 31/198* (2013.01); *A61K 31/592* (2013.01); *A61K 31/7004* (2013.01); *A61K 31/714* (2013.01); *A61K 33/00* (2013.01); *A61K 33/14* (2013.01); *A61K 33/24* (2013.01); *A61K 33/242* (2019.01); *A61K 33/243* (2019.01); *A61K 33/26* (2013.01); *A61K 33/34* (2013.01); *A61K 33/38* (2013.01); *A61K 33/42* (2013.01); *A61K 38/39* (2013.01); *A61N 1/40* (2013.01); *A61N 5/062* (2013.01); *A61N 5/0613* (2013.01); *A61N 5/0624* (2013.01); *A61Q 11/00* (2013.01); *A61Q 19/00* (2013.01); *A61K 2800/81* (2013.01); *A61N 5/067* (2021.08); *A61N 2005/063* (2013.01); *A61N 2005/0606* (2013.01); *A61N 2005/0651* (2013.01); *A61N 2005/0659* (2013.01); *A61N 2005/0663* (2013.01)

(58) Field of Classification Search
CPC .. A61K 2800/81; A61K 31/07; A61K 31/122; A61K 31/198; A61K 31/592; A61K 31/7004; A61K 31/714; A61K 33/00; A61K 33/14; A61K 33/24; A61K 33/242; A61K 33/243; A61K 33/26; A61K 33/34; A61K 33/38; A61K 33/42; A61K 38/39; A61K 8/20; A61K 8/24; A61K 8/368; A61K 8/416; A61K 8/44; A61K 8/442; A61K 8/65; A61Q 11/00; A61Q 19/00
See application file for complete search history.

(56) References Cited

U.S. PATENT DOCUMENTS

| | | | |
|---|---|---|---|
| 3,950,529 | A | 4/1976 | Fischer et al. |
| 5,002,051 | A | 3/1991 | Dew et al. |

(Continued)

FOREIGN PATENT DOCUMENTS

| | | |
|---|---|---|
| EP | 1224924 A2 | 7/2002 |
| TW | 469045 U | 1/2014 |

(Continued)

OTHER PUBLICATIONS

United States Patent and Trademark Office, Final Office Action issued in U.S. Appl. No. 16/349,222, dated Feb. 18, 2022, p. 9.

(Continued)

*Primary Examiner* — Lezah Roberts
(74) *Attorney, Agent, or Firm* — Pillsbury Winthrop Shaw Pittman LLP

(57) ABSTRACT

A method of treating diseased tissue while healing the wound using a diode laser which generates a beam of light having a wavelength in the visible portion of the electromagnetic spectrum (400 nm-700 nm) at a laser power of 0.001 to 1.2 watts, used with intermittent stops to control tissue temperature and biostimulate epithelial regeneration when used with or without substrates. A method of treating diseased tissue using a laser light in the green wavelength range (520-570 nm) at a laser power of 0.001 W to 5 W. A method of treating diseased tissue using a laser light in the IR wavelength range (700-1400 nm) at a laser power of 0.001 W to 5 W.

18 Claims, 32 Drawing Sheets

Related U.S. Application Data continuation-in-part of application No. 14/937,858, filed on Nov. 10, 2015, which is a continuation-in-part of application No. 13/864,226, filed on Apr. 16, 2013, now Pat. No. 9,180,319, which is a continuation-in-part of application No. 13/078,757, filed on Apr. 1, 2011, now abandoned.

(51) Int. Cl.

| | | |
|---|---|---|
| *A61C 1/00* | (2006.01) | |
| *A61K 31/198* | (2006.01) | |
| *A61K 8/368* | (2006.01) | |
| *A61K 31/592* | (2006.01) | |
| *A61K 8/65* | (2006.01) | |
| *A61Q 19/00* | (2006.01) | |
| *A61K 33/242* | (2019.01) | |
| *A61K 33/243* | (2019.01) | |
| *A61N 5/067* | (2006.01) | |

(56) References Cited

U.S. PATENT DOCUMENTS

| | | | |
|---|---|---|---|
| 5,130,997 | A | 7/1992 | Ortiz et al. |
| 5,292,362 | A | 3/1994 | Bass et al. |
| 5,391,550 | A | 2/1995 | Carniglia et al. |
| 5,464,436 | A | 11/1995 | Smith |
| 5,616,313 | A | 4/1997 | Williams et al. |
| 5,642,997 | A | 7/1997 | Gregg, II et al. |
| 6,221,068 | B1 | 4/2001 | Fried et al. |
| 6,878,145 | B2 | 4/2005 | Brugger et al. |
| 7,107,996 | B2 | 1/2006 | Ganz et al. |
| 7,621,745 | B2 | 11/2009 | Bornstein |
| 2003/0158111 | A1 | 8/2003 | Bar-Or |
| 2003/0232303 | A1 | 12/2003 | Black |
| 2004/0009598 | A1 | 1/2004 | Hench et al. |
| 2004/0199227 | A1 | 10/2004 | Altshuler et al. |
| 2004/0259053 | A1 | 12/2004 | Bekov |
| 2006/0210494 | A1 | 9/2006 | Rabiei et al. |
| 2006/0241495 | A1 | 10/2006 | Kurtz |
| 2007/0021807 | A1 | 1/2007 | Kurtz |
| 2008/0033514 | A1 | 2/2008 | Kurtz |
| 2008/0033515 | A1 | 2/2008 | Kurtz |
| 2008/0060148 | A1 | 3/2008 | Pinyayev |
| 2009/0087816 | A1 | 4/2009 | Bornstein |
| 2010/0029549 | A1 | 2/2010 | Chaput et al. |
| 2010/0076526 | A1 | 3/2010 | Krespi et al. |
| 2010/0098746 | A1 | 4/2010 | King |
| 2012/0251972 | A1 | 10/2012 | Kalmeta |
| 2012/0330288 | A1 | 12/2012 | Clementi et al. |
| 2013/0267943 | A1 | 10/2013 | Hancock |
| 2014/0074090 | A1 | 3/2014 | Lam et al. |
| 2014/0113243 | A1 | 4/2014 | Boutoussov et al. |
| 2014/0141389 | A1 | 5/2014 | Kalmeta |
| 2015/0164618 | A1 | 6/2015 | Heacock et al. |
| 2015/0283287 | A1 | 10/2015 | Agarwal et al. |
| 2016/0158284 | A1 | 9/2016 | Kalmeta |

FOREIGN PATENT DOCUMENTS

| | | |
|---|---|---|
| WO | 2007/027620 A1 | 3/2007 |
| WO | 2008/068749 A1 | 6/2008 |
| WO | 2011/096003 A1 | 8/2011 |
| WO | 2012130771 A1 | 10/2012 |
| WO | 2017083579 A1 | 5/2017 |

OTHER PUBLICATIONS

Koort et al., "A combined device for optimal soft tissue applications in laser dentistry", Laser Industry Report, Jan. 2013, pp. 24-29, vol. 4.

IP Australia, Examination Report issued in AU Patent Application No. 2020200444, dated May 24, 2021, pp. 1-6.

Schwarz et al., "The impact of laser application on periodontal and peri-implant wound healing", Periodontal 2000, Aug. 20, 2009, pp. 79-108, vol. 51.

Amorim et al., "Clinical study of the gingiva healing after gingivectomy and low-level laser therapy", Photomed Laser Surg., 2006, pp. 588-594, vol. 24(5).

Rodrigues et al., "Modulation of phosphate/pyrophosphate metabolism to regenerate the periodontium: a novel in vivo approach", J Periodontal, Dec. 2011, pp. 1757-1766, vol. 82(12).

European Patent Office, Extended European Search Report issued in EP Patent Application No. 17870468.0, dated Oct. 28, 2020, pp. 1-14.

Canadian Intellectual Property Office, Official Action issued in CA Patent Application No. 3,005,045, dated Mar. 31, 2020, pp. 1-4.

Asai et al. "Maxillary Sinus Augmentation Model in Rabbits" Effect of Occluded Nasal Ostium on New Bone Formation (2002) Clin. Oral Impl. Res. 13:405-409.

Goldstep—www.oralhealthjournal.com, "Diode Lasers for Periodontal Treatment: The story so far", Publication, Dec. 2009, p. 44-46.

Ozcelik, http://www.ncbi.nlm.nih.gov/pubmed/148081859, "Enamel matrix derivative and low-level laser therapy in the treatment of intra-bony defects: a randomized placebo-controlled clinical trial",—J. Clin. Periodontol., Feb. 2008, vol. 35(2), pp. 56-147., Epub Dec. 13, 2007.

United States Patent and Trademark Office, Official Action issued in U.S. Appl. No. 14/937,858, dated Jul. 11, 2022, pp. 1-6.

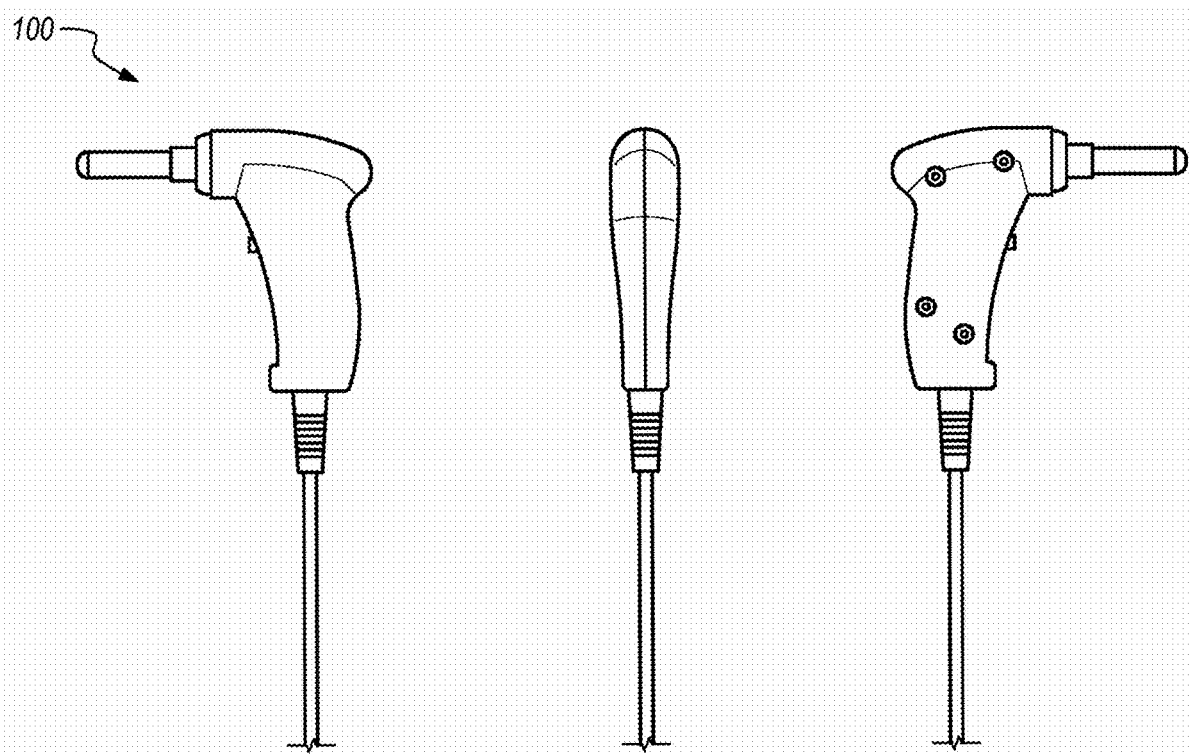
FIG. 17A  FIG. 17B  FIG. 17C
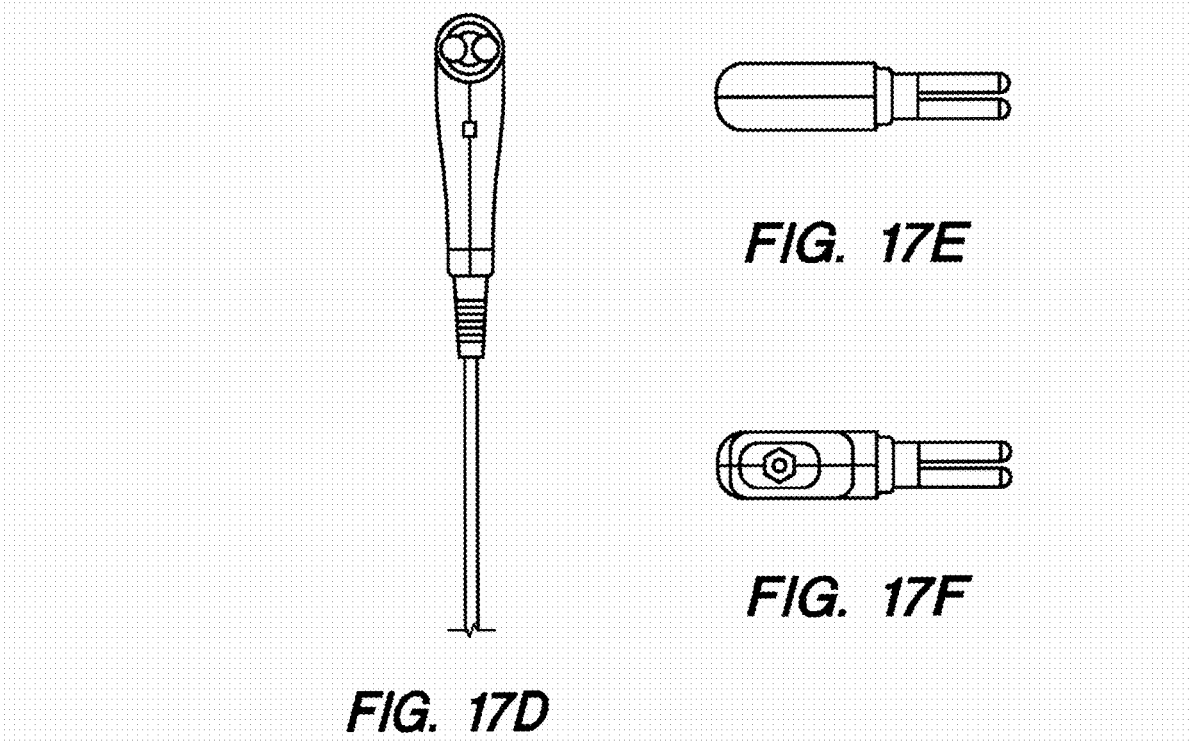
FIG. 17E
FIG. 17F
FIG. 17D

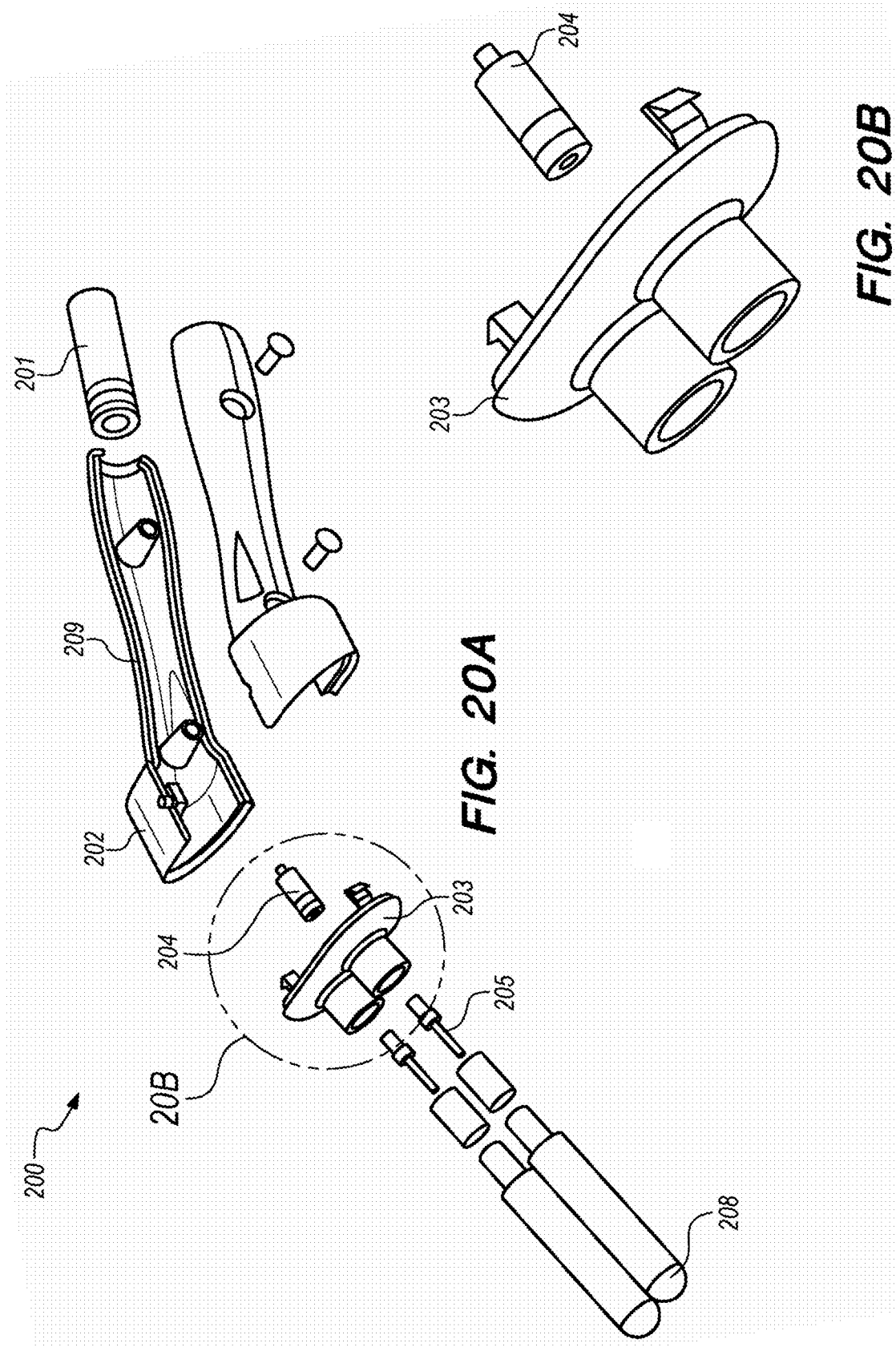

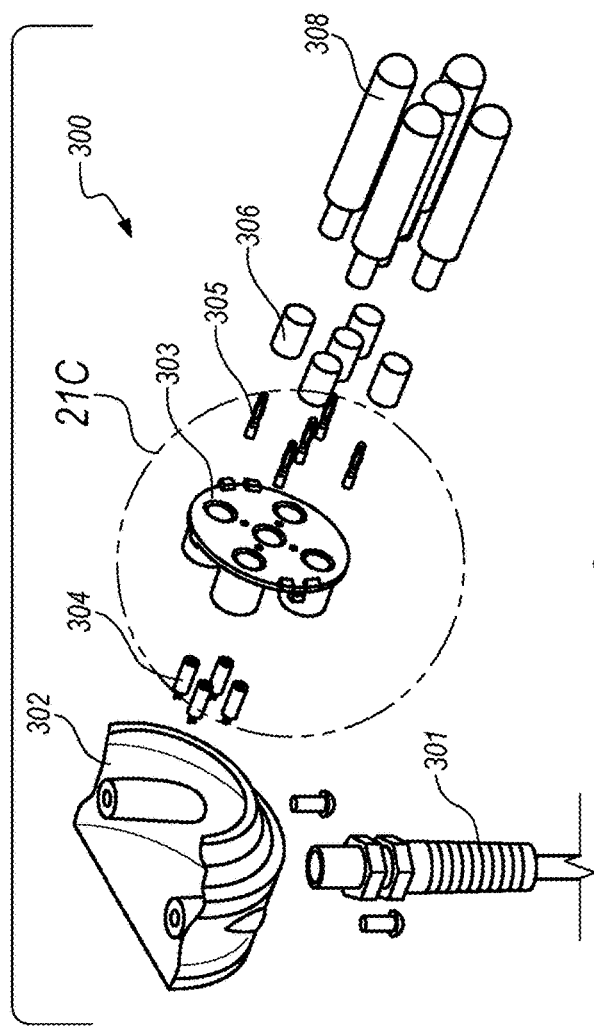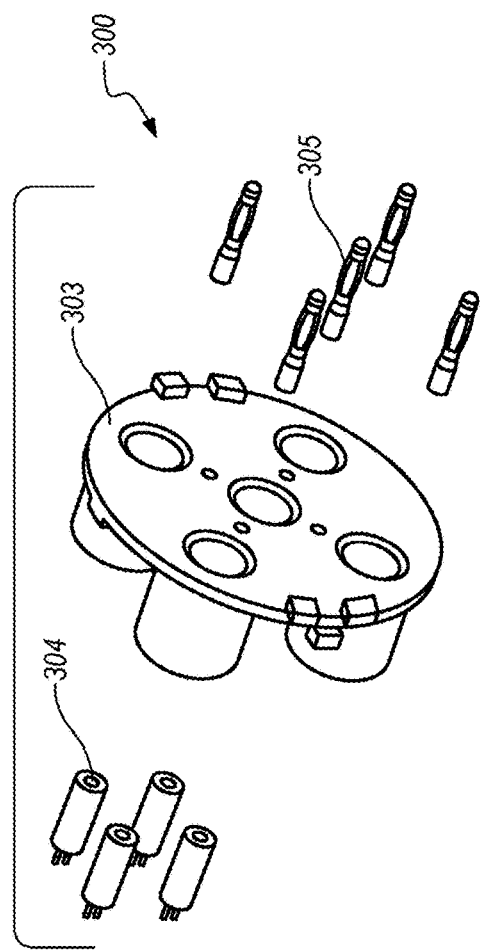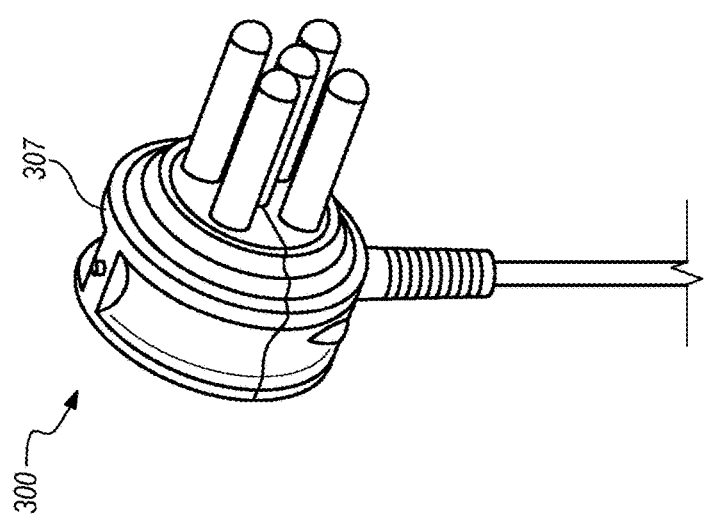

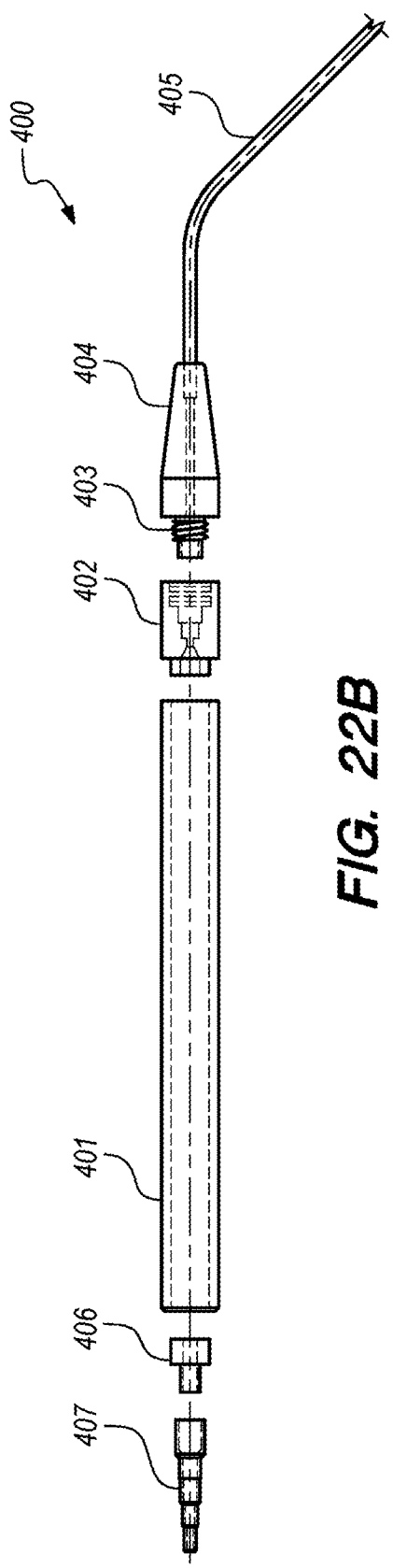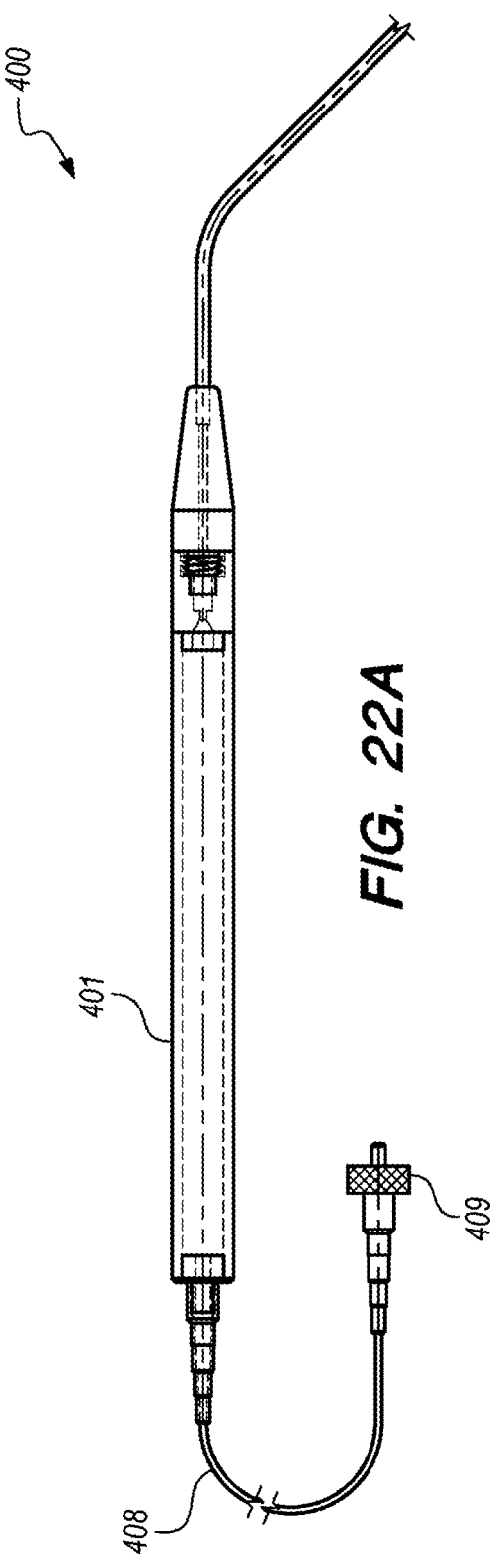
FIG. 22B
FIG. 22A

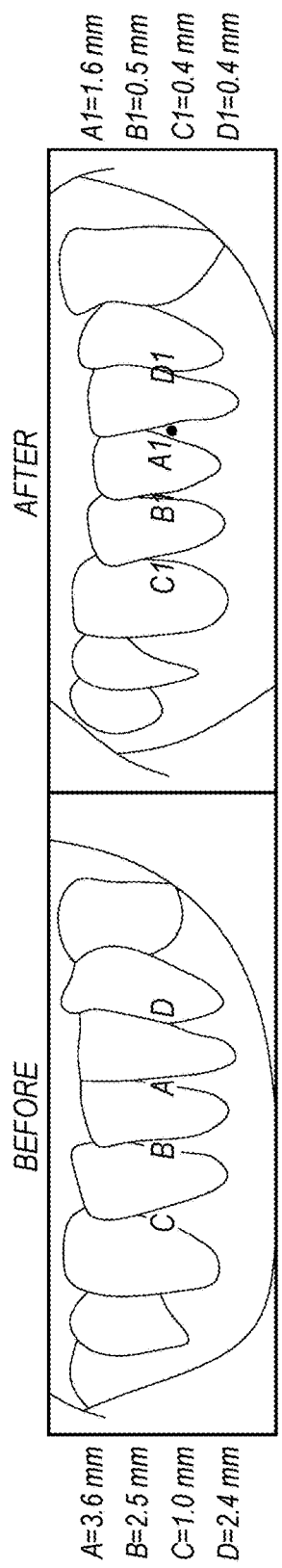
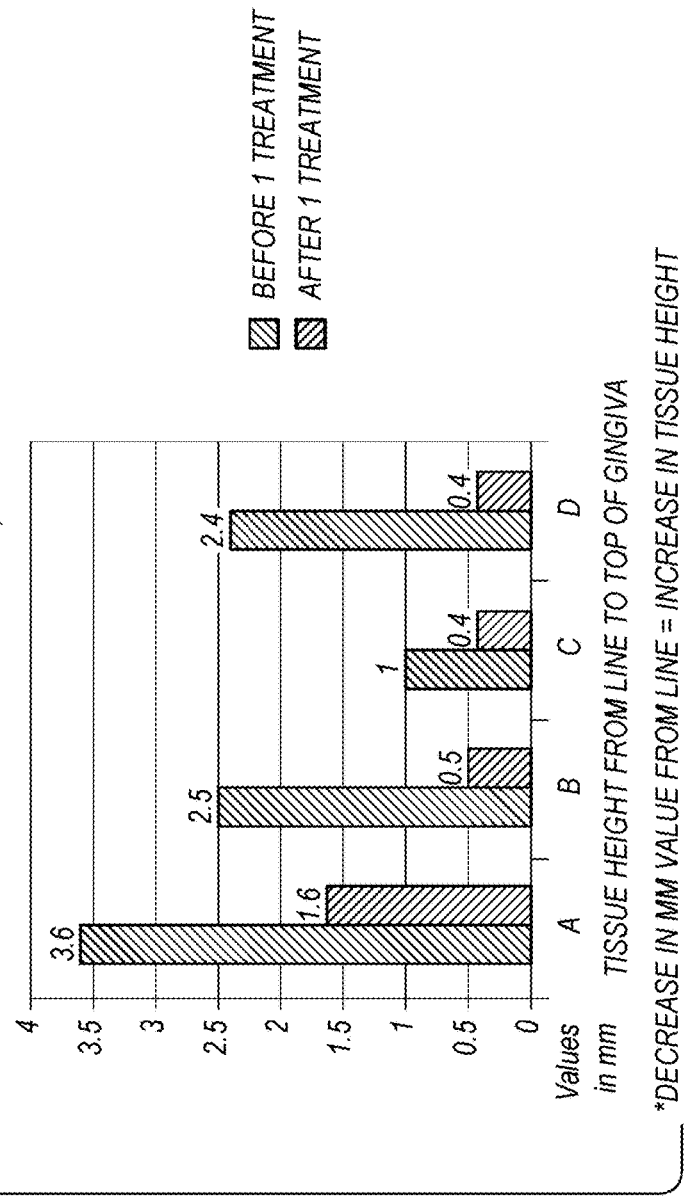
FIG. 26A
FIG. 26B
FIG. 26C

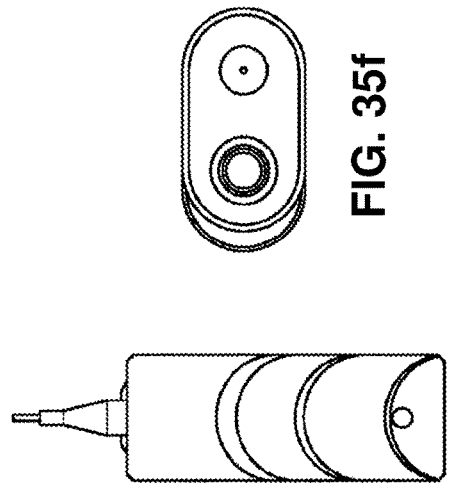
FIG. 35f
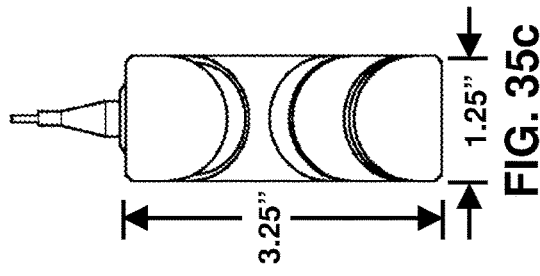
FIG. 35c
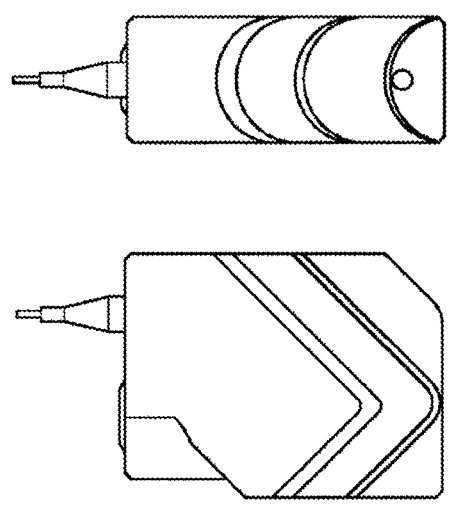
FIG. 35e
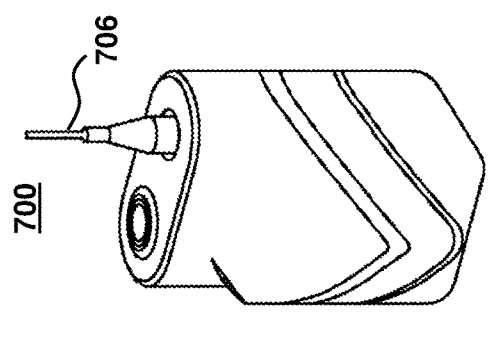
FIG. 35b
FIG. 35d
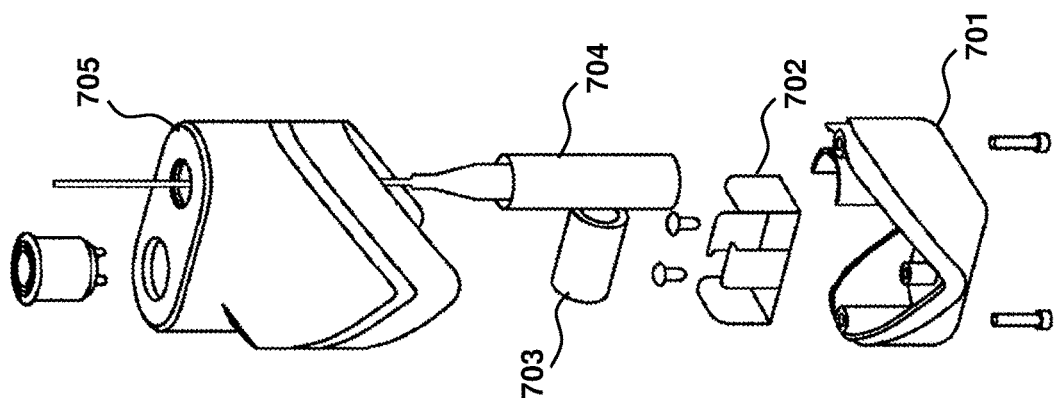
FIG. 35a

800

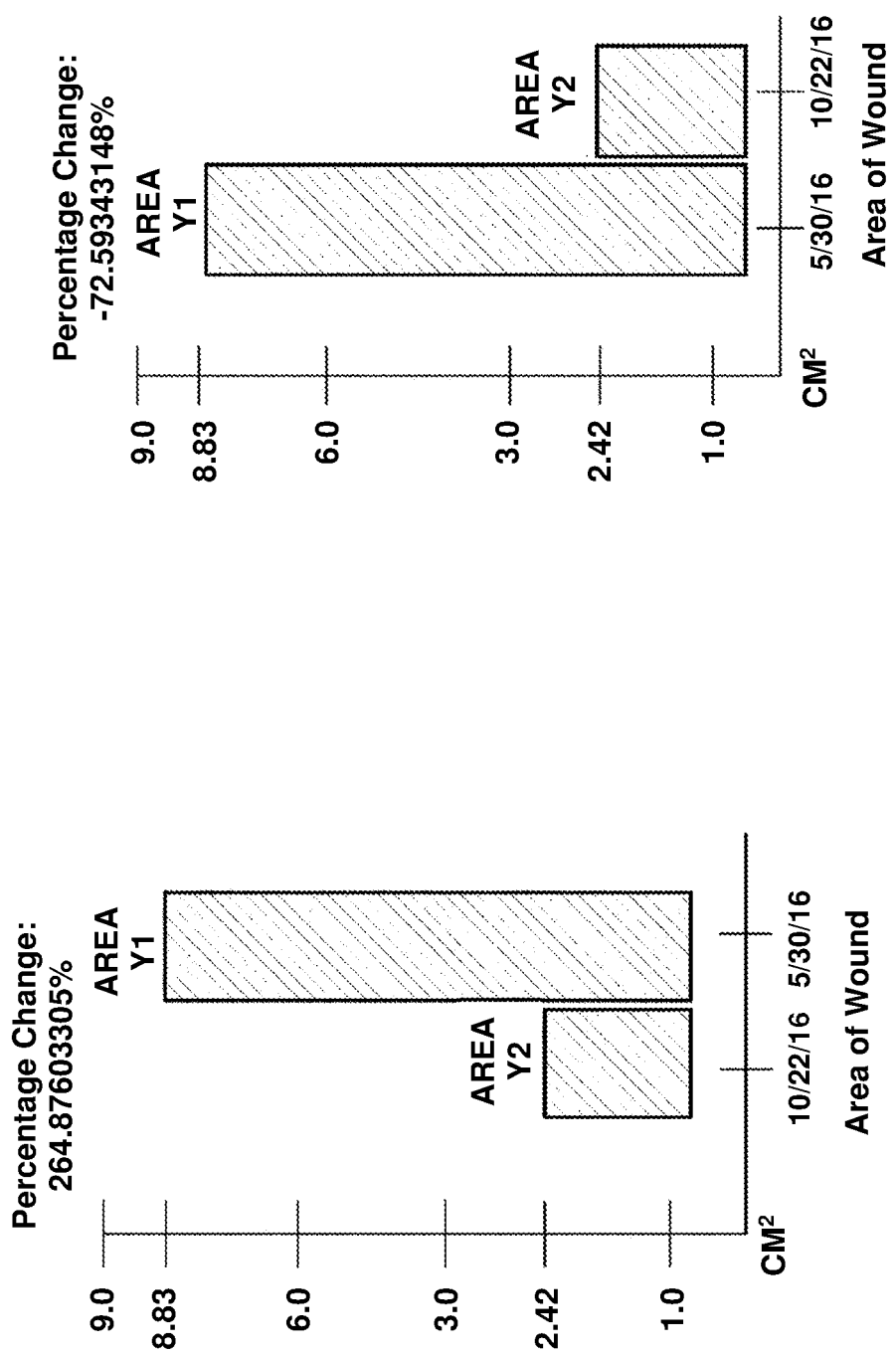

LASER ASSISTED WOUND HEALING PROTOCOL AND SYSTEM

RELATED PATENT APPLICATIONS

This application is a Continuation Patent Application claiming the benefit of priority under 35 U.S.C. 120 from U.S. patent application Ser. No. 15/348,793 filed Nov. 10, 2016 which claims the benefit of priority from U.S. patent application Ser. No. 14/937,858 filed Nov. 10, 2015 which claims the benefit of priority from U.S. patent application Ser. No. 13/864,226 filed Apr. 16, 2013, now issued U.S. Pat. No. 9,180,319, which claims the benefit of priority from U.S. patent application Ser. No. 13/078,757 filed Apr. 1, 2011, now abandoned, the entire contents of which are herein incorporated by reference.

FIELD OF THE INVENTION

The present invention relates generally to a method of treating gum diseases using a diode laser which produces a beam of light having a wavelength in the visible portion of the electromagnetic spectrum (400 nm-700 nm). Optionally, the laser light utilizes green wavelength range (520-570 nm) at a laser power 0.001 W to 5 W to treat wounds. It is also contemplated that described is a method of treating diseased tissue using a diode laser. Optionally, the laser light utilizes the IR wavelength range (700 nm-1400 nm) at a laser power of 0.001 W to 5 W to treat wounds. Optionally, an LED light utilizes the IR wavelength range to treat wounds.

BACKGROUND OF THE INVENTION

Laser Assisted Periodontium and Osseous Regeneration (LAPOR) is a protocol which is laser assisted with the use of a substrate such as but not limited the LAPOR periodontal solution, the LAPOR periodontal gel and the LAPOR substrate and thus causes an increase in cell attachment of epithelial cells, gingival fibroblasts, PDL fibroblasts and adhesion of osteogenic cells. Enhanced cell migration and proliferation appears to lead to accelerated wound fill rates in vitro using PDL fibroblasts, gingival fibroblasts and osteoblast-like cells.

A substrate such as the LAPOR periodontal solution, the LAPOR periodontal gel and the LAPOR substrate, used in the LAPOR protocol, stimulates total protein synthesis and the synthesis of specific extracellular matrix molecules. Studies that evaluate the bone remodeling regulation system indicate that proteins influence this regulation system, thus indicating an indirect involvement in the bone remodeling process. When used in conjunction with three specially formulated periodontal and wound healing substrates, and LAPOR gel root conditioner, LAPOR has shown to stimulate total tissue and bone synthesis, increase gingival attachment, gingival height, bone density, bone height thereby showing accelerated wound fill rates in vivo.

The diode laser used produces a beam of light having a wavelength in the visible portion of the electromagnetic spectrum (400 nm-700 nm). Optionally, a beam of light having a wavelength in the green wavelength range (520-570 nm) at a laser power of 0.5 to 1.2 W is used in the LAPOR protocol. It has been shown by the LAPOR protocol to biostimulate the healing and regenerative processes of the periodontium, including the biostimulation of new bone and its supporting elements. The diode laser used in the LAPOR protocol, biostimulates the healing response of the periodontium nonsurgically, and biostimulates the tissue regeneration of the periodontium, nonsurgically, and prevents long junctional epithelium from migrating downwards into the sulcus (a biomechanical aspect of tissue healing), thereby preserving the tissue height. A diode laser used in the LAPOR protocol helps a substrate such as but not limited to proteins to stimulate total protein synthesis and the synthesis of extracellular matrix molecules, nonsurgically.

Alternatively, the LAPOR protocol may use a beam of light having a wavelength in the green wavelength range (520-570 nm), red wavelength range (620-750 nm), or yellow wavelength range (570-590 nm) having an alternative wattage of 0.001 W to 5 W, preferably 0.002 W to 4 W, more preferably 0.003 W to 4 W, and most preferably 0.005 W to 2 W. The diode laser used helps the substrates stimulate total tissue and bone synthesis by biostimulating the healing response and bone/tissue regeneration and its supporting elements of the wound.

It is further contemplated that the invention may be used to treat tissue damage and wounds, i.e. Laser Assisted Tissue and Osseous Regeneration (LATOR) using a solution, LATOR gel and LATOR substrate to enhance cell migration and proliferation leading to accelerated wound fill rates. The protocol is used in conjunction with six specially formulated tissue and wound healing substrates and a gel conditioner to stimulate total tissue and bone synthesis, increase tissue attachment, tissue height, bone density and bone height thereby showing accelerated would fill rates like the LAPOR protocol.

SUMMARY OF THE INVENTION

In an exemplary embodiment of the present invention, there is disclosed a method of treating wounds, including gum disease and gingival tissues post scaling/root planning, using a diode laser which generates a beam of light having a wavelength in the visible portion of the electromagnetic spectrum (400 nm-700 nm). Optionally, a beam of light having a wavelength in the green range (520-570 nm) at a laser power of 0.5 to 1.2 watts is used to decontaminate the gum tissue and to biostimulate healing and regenerate the periodontium (including cementum of the root surface), thus preventing long junctional epithelium from migrating downwards into the sulcus and thereby preserving the tissue height. Alternatively, a beam of light having a wavelength in the green wavelength range (520-570 nm), red wavelength range (620-750 nm), or yellow wavelength range (570-590 nm) having an alternative wattage of 0.001 W to 5 W may be used to biostimulate healing and regenerate the wound site, its tissue and bone. In a preferred embodiment, the wattage is in the range of 0.002 W to 4 W, more preferred in the range of 0.003 to 3 W, and most preferred in the range of 0.005 W to 2 W. A diode laser also biostimulates the healing and regenerative response induced by a substrate, i.e. the LAPOR periodontal and wound healing solution, the LAPOR periodontal gel and the LAPOR periodontal and wound healing substrates, the method comprising: 1) placing the laser inside the sulcus; 2) penetrating the entire sulcus by moving the laser light intermittently vertically and horizontally throughout the sulcus; and 3) placing the substrate in the sulcus prior to a blood clot forming (which then increases cell attachment, adhesion, migration and proliferation). In a preferred embodiment, the LATOR protocol may use a diode laser per the above parameters to treat general wound sites. Optionally, the laser light utilizes the IR wavelength range (700 nm-1400 nm) at a laser power of 0.001 W to 5 W to treat wounds.

In an alternative embodiment, the LAPOR protocol may use an LED light to biostimulate healing and regenerate periodontium and general wound tissue (LATOR protocol). The LED light is used at 10 W or lower on wounds to assist in new cell organization and hence tissue regeneration. Optionally, an LED light utilizes the IR wavelength range to treat wounds. Optionally, the laser light utilizes the IR wavelength range (700 nm-1400 nm) at a laser power of 0.001 W to 5 W to treat wounds.

In an alternative embodiment, the LAPOR and LATOR protocols may use a radiofrequency (RF) wave to decontaminate the gum tissue and biostimulate healing and regenerate the periodontium. The RF beam is used at 10 W or lower on wounds to assist in new cell organization and hence tissue regeneration. A carrier wave (sine wave) transports a non-sinusoidal waveform to the treatment location. The carrier wave frequency may be in the range of 0.1 MHz to 20 MHz while the non-sinusoidal waveform may be in the range of 0 to 40 KHz or alternatively 0-24 GHz. In a preferred embodiment, the carrier wave frequency is in the range of 0.2 MHz to 10 MHz, preferably 0.3 MHz to 5 MHz. Optionally the 0.001 W to 10 watt range, preferably a 0.001 W to 3 W range, is utilized in the hertz range of 40 Hz to 24 GHz. In a further alternative embodiment, the RF wave is a single sine wave. In a further alternative embodiment, the RF wave is more than one sine wave wherein the more than one demonstrates a harmonics pattern. In a preferred embodiment, the LATOR protocol may use an RF wave per the above parameters to treat general wound sites. Optionally, the non-sinusoidal waveform may be in the range of the above parameters in the absence of a carrier wave.

In another embodiment of the present invention, there is disclosed a root/bone/cartilage conditioner comprised of EDTA 15%, calcium gluconate 20%, methylparaben, propylparaben, Ethanolamine as a buffering agent, carboxymethylcellulose, and green food coloring and sterile water.

In still another embodiment of the present invention, there is disclosed a first substrate comprised of: a combination of mono or disodium phosphate and sodium hydroxide in solution with a sodium content of 11 mg/100 g; 60% water; 9% Lysine; 9% Proline; 9% all other essential amino acids wherein the amino acids are chosen from the group consisting of Isoleucine, Leucine, Methionine, Phenylalanine, Threonine, Tryptophan, Valine, Histadine, Asparagine and Selenocysteine; 2% of all other non-essential amino acids wherein the amino acids are chosen from the group consisting of Alanine, Arginine, Aspartate, Cysteine, Glutamate, Glutamine, Glycine, Serine, Tyrosine and Pyrrolsine; 6.9% free bases wherein the free bases are chosen from the group consisting of adenosine, uridine, guanosine, iridin and cytidine; 2% phosphates wherein the phosphates are chosen from the group consisting of ADP, ATP and acetycholine; and 1% benzoic acid.

In still another embodiment of the present invention, there is disclosed a second substrate comprised of: tricalcium phosphate wherein the tricalcium phosphate is precipitated with calcium hydroxide/Claw oil; and hydroxyapatite crystals.

In yet another embodiment of the present invention, there is disclosed a third substrate comprised of: 5.1% hyaluronic acid; 8% fatty acids wherein the fatty acids are chosen from the group consisting of Linoleic acid (LA), alpha-linolenic acid (ALA), 4.4% sugars wherein the sugars are chosen from the group consisting of mannose, galactose, N-acetyl-lactosamine, N-acetylglucosamine, N-acetylneuraminic acid, fucose (L configuration minus a carboxyl group at the 6 position), and xylose; 2.2% mixture of glucose and fucose (L configuration minus a carboxyl group at the 6 position); 3% lipids wherein the lipids are chosen from the group consisting of vitamin A, vitamin D2, D3, vitamin E, vitamin K1, K2, vitamin B12 (methylcobalamin, hydroxocobalamin), cholesterol, and diaglycerol; 2.7% vitamins wherein the vitamins are chosen from the group consisting of vitamin B1, vitamin B2, vitamin B3, vitamin B5, vitamin B6, vitamin B7, vitamin B9, vitamin C and pantothenic acid; 4.5% electrolyte sources: wherein the electrolyte sources are chosen from the group consisting of Calcium Chloride, Choline Chloride, Magnesium Sulfate, Potassium Chloride, Potassium Phosphate (monobasic), Sodium Bicarbonate, Sodium Chloride, and Sodium Iodide; 6% metals wherein the metals are chosen from the group consisting of Ag nanoparticles and Au nanoparticles; 3.9% ionic metals wherein the ionic metals are chosen from the group consisting of copper, zinc, selenium, iron, manganese, cobalt, chromium, boron, and molybdenum; and 4% other ionic metals wherein the other ionic metals are chosen from the group consisting of boron, silicon, nickel and vanadium.

In another embodiment of the present invention, there is disclosed a fourth substrate comprised of carbomer, potassium chloride, chloride, sodium, potassium, manganese, calcium tri-phosphate, sulfate, carbonate, snail serum, snail secretion filtrate, HA, Au, Ag, Cu, Fe, Pt, collagen, glyceine HCl and fucose.

In another embodiment of the present invention, there is disclosed as fifth substrate comprised of a tricalcium phosphate and/or collagen limed and/or collagen unlimed.

In another embodiment of the present invention, there is disclosed a sixth substrate comprised of tricalcium phosphate and/or collagen limed and/or collagen unlimed and/or HCl and/or NaCl, and/or metals wherein the metals are chosen from the group consisting of copper, Au, Ag, iron and platinum or any combination thereof.

The more important features of the invention have thus been outlined in order that the more detailed description that follows may be better understood and in order that the present contribution to the art may better be appreciated. Additional features of the invention will be described hereinafter and will form the subject matter of the claims that follow.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways.

Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The foregoing has outlined, rather broadly, the preferred feature of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention and that such other structures do not depart from the spirit and scope of the invention in its broadest form.

BRIEF DESCRIPTION OF THE DRAWINGS

Other aspects, features, and advantages of the present invention will become more fully apparent from the following detailed description, the appended claim, and the accompanying drawings in which similar elements are given similar reference numerals.

FIG. 8 shows an X-Ray view of the upper teeth before treatment with a diode laser after treatment with a substrate.

FIG. 9 shows an X-ray view of the upper teeth of FIG. 8 after treatment with a diode laser after treatment with a substrate.

FIG. 17a-17f show various views of a first embodiment of a diode laser of the present invention. (a) shows a right side view. (b) shows a back side view. (c) shows a left side view. (d) shows a front side view. (e) shows a top view. (f) shows a bottom view.

FIGS. 20a and 20b an exploded view of the diode laser of FIG. 19. (a) shows an exploded view. (b) shows a close-up of the laser housing.

FIG. 21a-21c show various view of a third embodiment of the diode laser of the present invention. (a) shows a side perspective view. (b) shows an exploded view. (c) shows a close-up view of the laser housing.

FIG. 22a-22c shows a fiber optic laser of the present invention. (a) shows an assembled view. (b) shows an exploded view. (c) shows a fully assembled laser.

FIG. 26a-26c show gingival wound healing and tissue regeneration measurements before and after treatment. (a) shows wounds before treatment. (b) shows tissue regeneration after treatment. (c) shows tissue height measurements before and after treatment.

FIG. 35a-35f show various views of a laser power source for the fiber optic hand piece and interchangeable tips.

FIG. 40 shows ankle epithelial wound regeneration before and after treatment.

FIG. 41 shows ankle wound size reduction before and after treatment.

DETAILED DESCRIPTION OF THE INVENTION

Definitions

Figure 1:
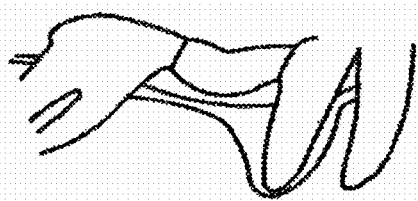
FIG. 1 shows an X-Ray view of a patient's teeth before treatment with a diode laser before a substrate has been applied.
Figure 2:
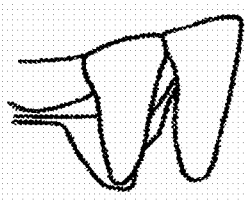
FIG. 2-7 show X-Ray views of the lower teeth of FIG. 1 after treatment with a diode laser after treatment with a substrate.
Figure 3:
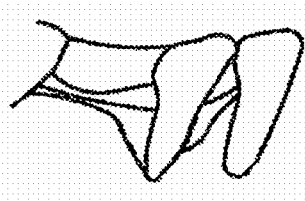
Figure 4:
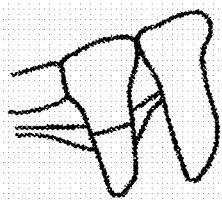
Figure 5:
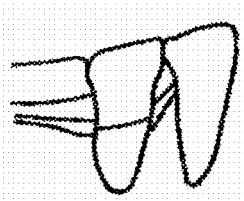
Figure 6:
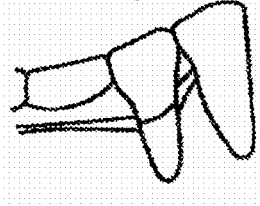
Figure 7:
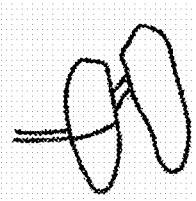

As used herein, the term "gum disease" means periodontal disease which can lead to tooth loss and/or other health problems. Examples of periodontal disease include gingivitis, aggressive periodontitis, chronic periodontitis, periodontitis as a manifestation of systemic diseases, and necrotizing periodontal disease.

As used herein, the term "tissue disease" means tissue and/or epithelial loss due to injury and/or wounds which can lead to other health problems such as amputation of limbs.

As used herein, the term "patient" means any individual suffering from a disease of the gums and in need of treatment for said gum disease.

As used herein, the term "locus" means an exact point of measurement within the sulcus or the immediate surrounding area.

As used herein, the term "substrate mixture" means the mixture of the first substrate and/or the second substrate and/or the third substrate and/or the fourth substrate and/or the fifth substrate and/or sixth substrate disclosed herein for treatment of gum disease and/or tissue disease and/or wounds.

As used herein, the term "bone regeneration" means increasing the density of calcium at specific loci in or around the sulcus.

As used herein, the term "calcium density" means the measurement of calcium mass around a given loci.

As used herein the term "wound" means any area that has lost any original tissue or bone or any other structure not named that lost a healthy non-wounded, undamaged and unaged form.

The LAPOR protocol can be used in the treatment of gum disease and wounds by combining the most effective methods of treatment with the use of a special laser. Approximately 66% of the United States population has some form of gum disease. But many avoid seeking treatment because of the discomfort that often results from gum surgery. LAPOR provides a new choice. The LAPOR protocol is a treatment that is more effective as traditional periodontal surgery, and it is much more beneficial to the patient both in the short term and in the long run. The LATOR protocol can similarly be used for treatment of tissue disease and wounds.

The LAPOR protocol takes only about an hour and only two short follow-up visits. Patients enjoy no downtime with recovery taking only 24 hours. This makes immediate return to work both possible and comfortable.

After having the LAPOR protocol performed, gum recession is zero when compared to that which most often follows normal periodontal surgery. This, combined with new cementum formation on the roots, bone formation in previous defects, periodontal ligament formation and no tooth loss. After having the LATOR protocol performed, wound fibrosis is zero compared to that which most often follows normal treatment, new tissue formation occurs multi directionally and the wound closes without grafting.

The LAPOR protocols of the present invention can be used to heal wound sites by combining or using separately the most effective methods of treatment with the laser, LED, radiofrequency energy and substrates. Following performance of treatment protocols, no receding of tissue from the wound site was observed. In a preferred embodiment, the RF energy waves may be up to 10 W. The carrier wave frequency may be in the range of 0.1 MHz to 20 MHz while the non-sinusoidal waveform may be in the range of 0 to 40 KHz or from 0 to 24 GHz. In a preferred embodiment, the carrier wave frequency is in the range of 0.2 MHz to 10 MHz, preferably 0.3 MHz to 5 MHz. Optionally a 0.001 W to 10 W range RF energy, preferably a 0.001 W to 3 W range, is utilized in the hertz range of 40 Hz to 24 GHz. In a further alternative embodiment, the RF wave is more than one sine wave wherein the more than one demonstrates a harmonics pattern.

The special type of laser used in the LAPOR protocol and the LATOR protocol is the diode, a semiconductor coherent light beam used on s. The laser light used has a wavelength in the visible portion of the electromagnetic spectrum, between 400 nm-700 nm wavelength. Optionally, the green range (520-570 nm) of the visible spectrum is utilized at a laser power of 0.5 to 1.2 watts, which disinfects the site, leaving the gum tissue bacteria free, and biostimulates healing; in conjunction with treatment with a substrate, the laser biostimulates regeneration of the periodontium. Traditional periodontal therapy removes tissue height of a tooth to reduce the pocket depths. The LAPOR protocol is a regenerative procedure. The patient does not lose tissue volume. Tissue volume is increased and bone is regenerated. For general tissue disease, the laser biostimulates regeneration of tissue where traditional therapy removes tissue height to reduce the disease. Optionally, the laser light utilizes the IR wavelength range (700 nm-1400 nm) at a laser power of 0.001 W to 5 W to treat wounds. Optionally, LED light is used at 10 W or lower.

The use of the diode laser in conjunction with routine scaling and root planning is more effective than scaling and root planning alone. It enhances the speed and extent of the patients gingival healing and postoperative comfort. This is accomplished through laser bacterial reduction and biostimulation with a laser light having a wavelength in the visible portion of the electromagnetic spectrum, between 400 nm-700 nm wavelength. Optionally, the green range (520-570 nm) of the visible spectrum is utilized at a laser power of 0.5 to 1.2 watts. Alternatively, the laser power wattage may be in the range of 0.001 W to 5 W, preferably 0.002 W to 4 W, more preferably 0.003 W to 3 W, and most preferably 0.005 W to 2 W.

Figure 10:
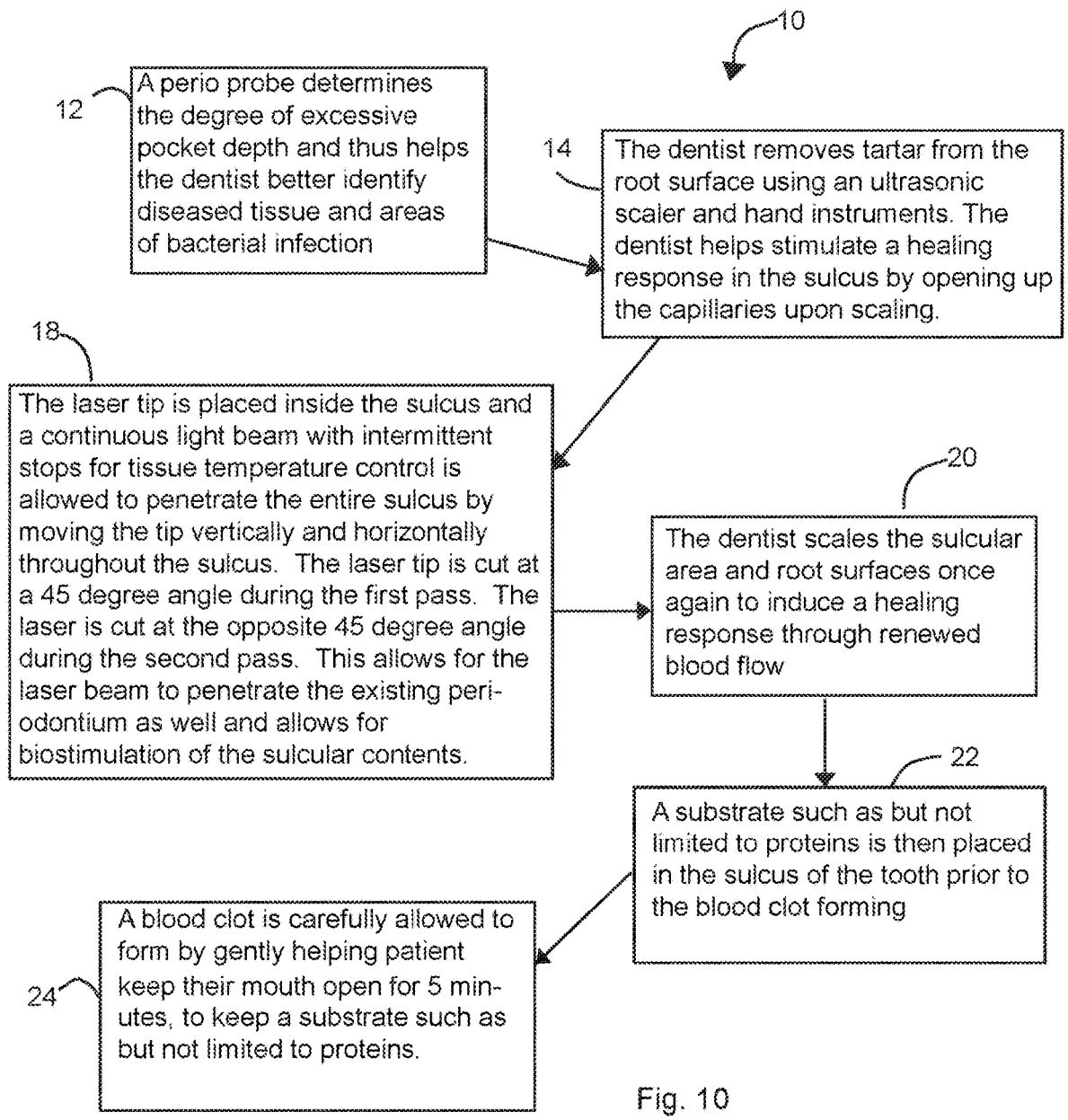
FIG. 10 shows a flow diagram of a method of using a diode laser to treat gum disease in accordance with the principles of the invention.

Referring to FIG. 10, there is disclosed a method 10 of using a diode laser which produces a beam of light, used intermittently, having a wavelength in the visible portion of the electromagnetic spectrum, between 400 nm-700 nm wavelength. Optionally, the green range (520-570 nm) of the visible spectrum is utilized at a laser power of 0.5 to 1.2 watts to treat gum disease. Starting at block 12, a perio probe determines the degree of excessive pocket depth and thus helps the dentist better identify diseased tissue and areas of bacterial infection. The dentist removes calculus from the root surface using an ultrasonic scaler and hand instruments, block 14. This action by the dentist helps stimulate a healing response in the sulcus by opening the capillaries upon scaling. Going to block 18, the laser tip is placed inside the sulcus and a continuous light beam with intermittent stops for tissue temperature control is allowed to penetrate the entire sulcus by moving the tip vertically and horizontally throughout the sulcus. The laser tip is cut at a 45 degree angle during the first pass. The laser is cut at the opposite 45 degree angle during the second pass. This allows for the laser beam to penetrate the existing periodontium to decontaminate the tissue, as the heat of the targeted laser light kills the bacteria. This also allows for biostimulation of the sulcular contents. At block 20, the dentist scales the sulcular area and root surfaces once again to induce a healing response through renewed blood flow. Going to block 22, at least one substrate, such as but not limited to matrix proteins, is then placed in the sulcus of the tooth prior to the blood clot forming and at block 24, a blood clot is carefully allowed to form by gently helping patient keep their mouth open for 5 minutes, to keep the substrate intact. Optionally, the laser light utilizes the IR wavelength range (700 nm-1400 nm) at a laser power of 0.001 W to 5 W to treat wounds.

Alternatively, the laser tip is a specially designed tip that disperses light energy throughout the wounded sulcus which allows the laser beam to penetrate the existing tissues to decontaminate the tissue, as the heat of the targeted laser light kills the bacteria and as a result block 20 may be eliminated going directly to block 22

The LAPOR protocol is much less invasive than traditional surgery and offers advantages and benefits over its counterpart. Recovery time is much faster because most, if not all, damage to healthy tissue is avoided through the use of more advanced technology. Because the LAPOR protocol leaves healthy tissue intact, the height of the gums themselves increases around the teeth and is better preserved. The LAPOR protocol prevents long junctional epithelium from migrating downwards into the sulcus, thus preserving the tissue height and allowing for the regeneration of the periodontium.

Figure 18A:
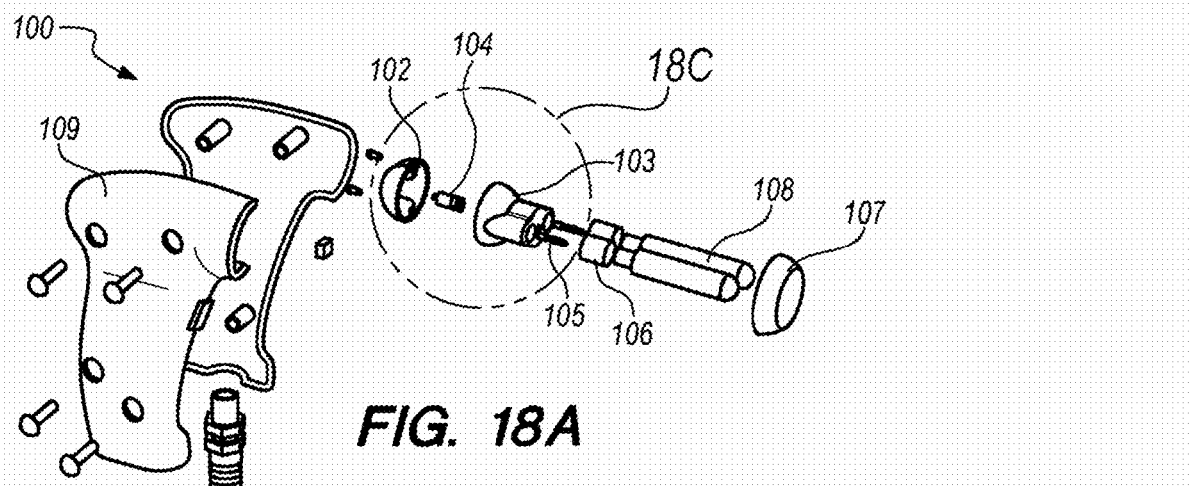
FIG. 18a-18c show an exploded view of the diode laser of FIG. 17. (a) shows an exploded view. (b) shows an assembled view. (c) shows a close-up of the laser housing.
Figure 18B:
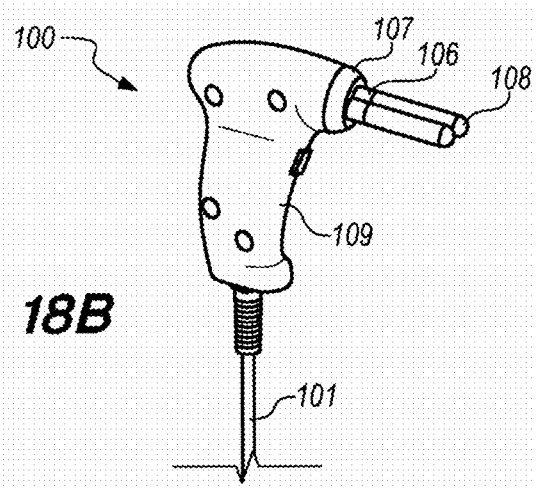
Figure 18C:
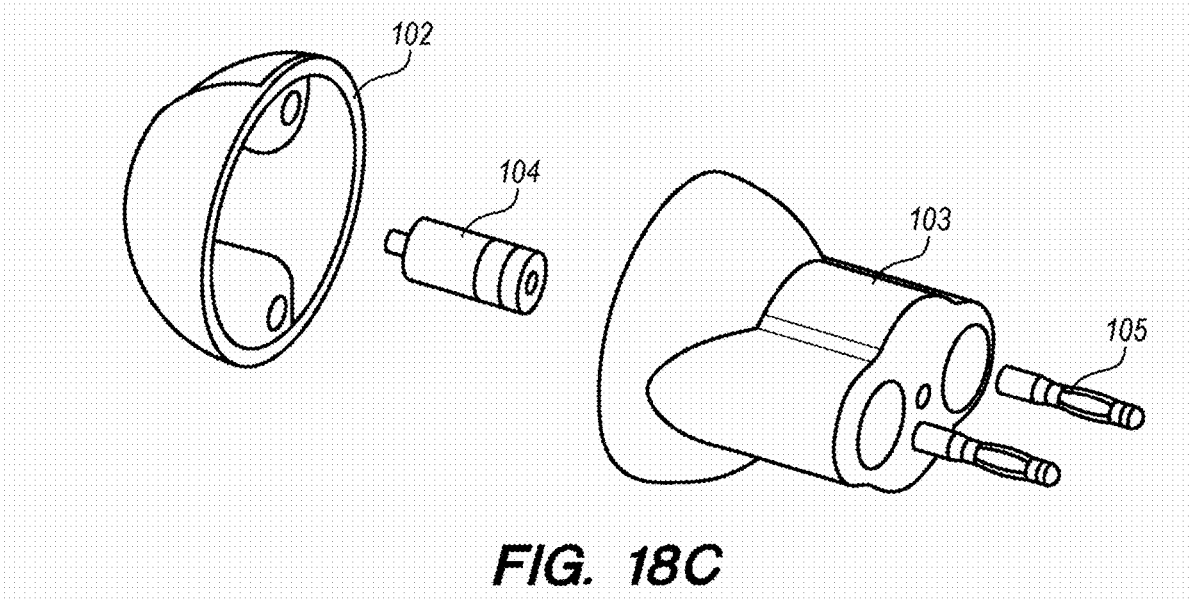
Figure 19A:
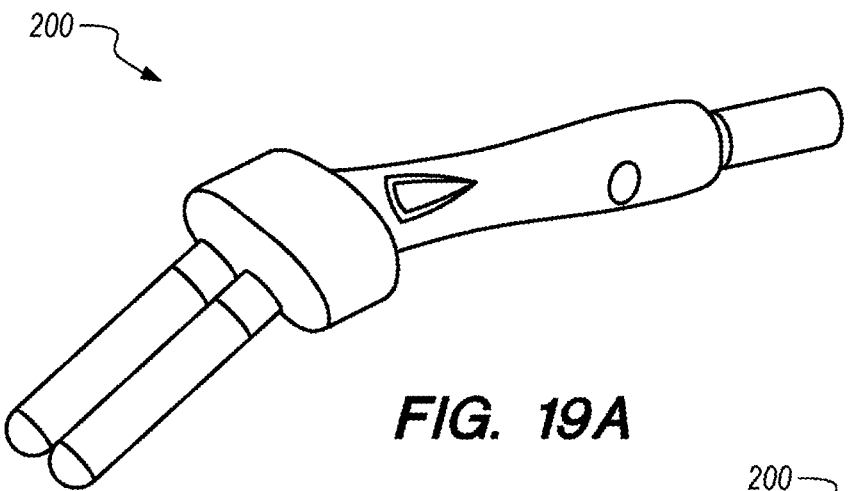
FIG. 19a-19g shows various views of a second embodiment of a diode laser of the present invention. (a) shows a top perspective view. (b) shows a back view. (c) shows a left side view. (d) shows a top view. (e) shows a front perspective view. (f) shows a right side view. (g) shows a bottom view.
Figure 19B:
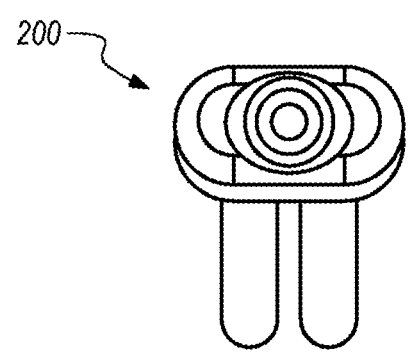
Figure 19C:
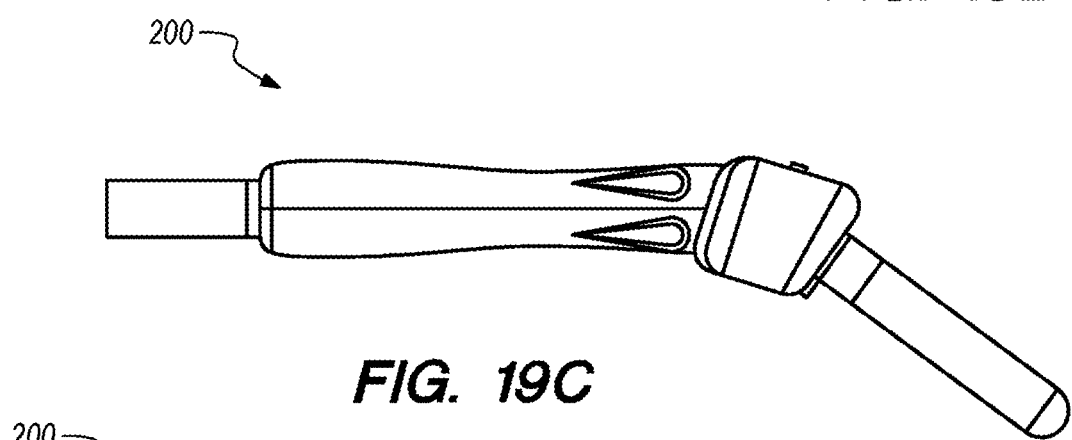
Figure 19D:
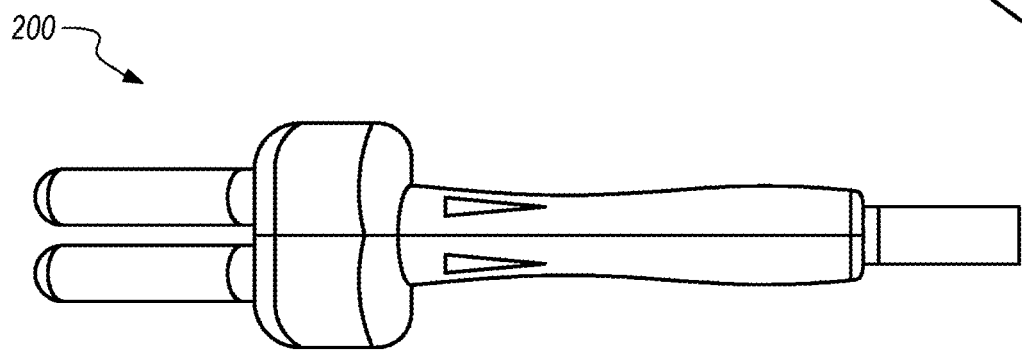
Figure 19E:
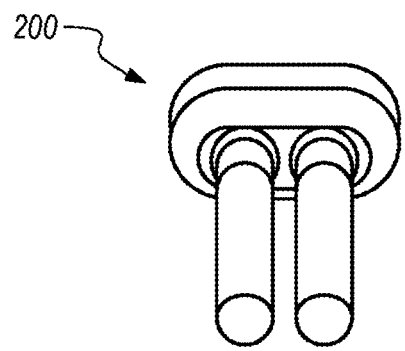
Figure 19F:
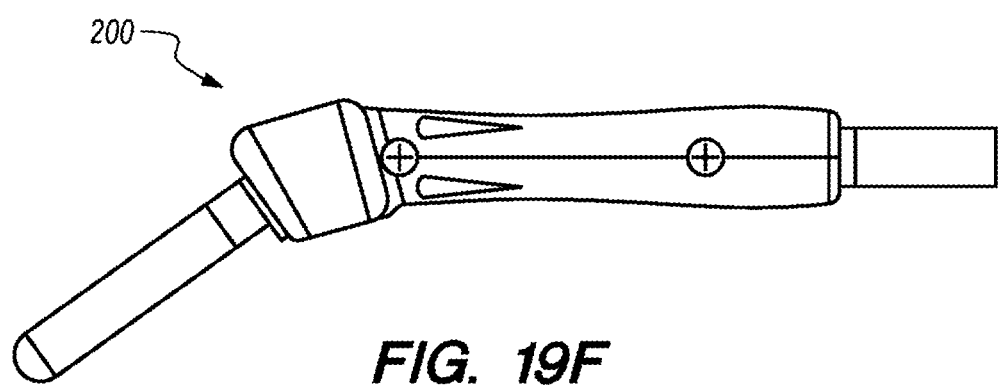
Figure 19G:
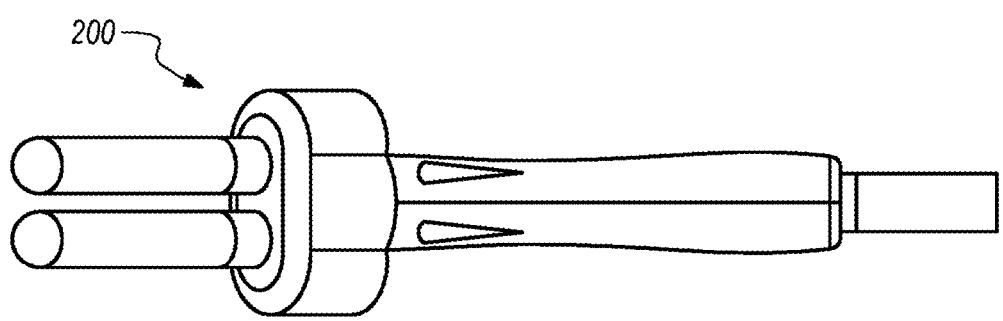

Referring to FIG. 17a-17f, shown are various angles of the first embodiment of a device 100 for use in conjunction with the substrates and methods of the present invention. FIG. 18a and 18b show perspective views of the device 100 in the first embodiment. Specifically, FIG. 18a illustrates an exploded view of the device 100 comprised of cord 101 integrally connected to handle 109, handle 109 further connected to heat sink 102. Housing 103 securely connects to heat sink 102 thereby creating a cavity between the housing 103 and heat sink 102. Laser 104 is positioned within the cavity between housing 103 and heat sink 102. Male connectors 105 connect RF source 108 to housing 103 wherein threaded inserts 106 cover the connection therebetween. Cap 107 is positioned over housing 103 and secures to handle 109. FIG. 18c shows a detailed view of heat sink 102, laser 104, housing 103 and male connectors 105 in relation to each other. In a preferred embodiment, the device 100 may have a plurality of RF sources 108 wherein a plurality is defined as at least two tips (i.e. dipole). Housing 103 is capable of movement such that RF source 108 may be adjusted 45° up or down relative to the x-axis for ease of use depending upon the location of the wound receiving treatment.

The laser energy may have wavelength in the green wavelength range (520-570 nm), red wavelength range (620-750 nm), or yellow wavelength range (570-590 nm) having a wattage of 0.001 W to 5 W. In a preferred embodiment, laser energy has a wattage of 0.001 W to 5 W. The wattage is in the range of 0.001 W to 4 W, more preferred in the range of 0.003 to 3 W, and most preferred in the range of 0.005 W to 2 W. The RF energy may have a power of 10 watts or lower. The carrier wave frequency may be in the range of 0.1 MHz to 20 MHz while the non-sinusoidal waveform may be in the range of 0 to 40 KHz or from 0 to 24 GHz. In a preferred embodiment, the carrier wave frequency is in the range of 0.2 MHz to 10 MHz, preferably 0.3 MHz to 5 MHz. Optionally a 0.001 W to 10 W range RF energy, preferably a 0.001 W to 3 W range, is utilized in the hertz range of 40 Hz to 24 GHz. In a further alternative embodiment, the RF wave is more than one sine wave wherein the more than one demonstrates a harmonics pattern. Optionally, the non-sinusoidal waveform may be in the range of the above parameters in the absence of a carrier wave.

Referring to FIG. 19a-19g, shown are various angles of a second embodiment of a device 200 for use in conjunction with the substrates and methods of the present invention. FIG. 20a shows a perspective view of the device 200 of the second embodiment. Specifically, FIG. 20a illustrates an exploded view of the device 200 comprised of wire grommet 201 integrally connected to handle 209, handle 209 further comprised of heat sink 202. Housing 203 securely connects to heat sink 202 thereby creating a cavity between the housing 203 and heat sink 202. Laser 204 is positioned within the cavity between housing 203 and heat sink 202. Male connectors 205 connect RF source 208 to housing 203 wherein threaded inserts 206 cover the connection there between. FIG. 20b shows a detailed view of laser 204 and housing 203 in relation to each other.

Referring to FIG. 21a-21c, shown is a third embodiment of a device 300 for use in conjunction with the substrates and methods of the present invention. FIG. 21a shows a perspective view of the device 300 of the second embodiment. Specifically, FIG. 21b illustrates an exploded view of the device 300 comprised of wire grommet 301 integrally connected to housing 303, housing 303 further comprised of heat sink 302. Housing 303 securely connects to heat sink 302 thereby creating a cavity between the housing 303 and heat sink 302. Laser 304 is positioned within the cavity between housing 303 and heat sink 302. Male connectors 305 connect RF source 308 to housing 303 wherein threaded inserts 306 cover the connection there between. FIG. 21c shows a detailed view of laser 304 and housing 303 in relation to each other. By way of example only, the device may have five or six tips.

Figure 22C:
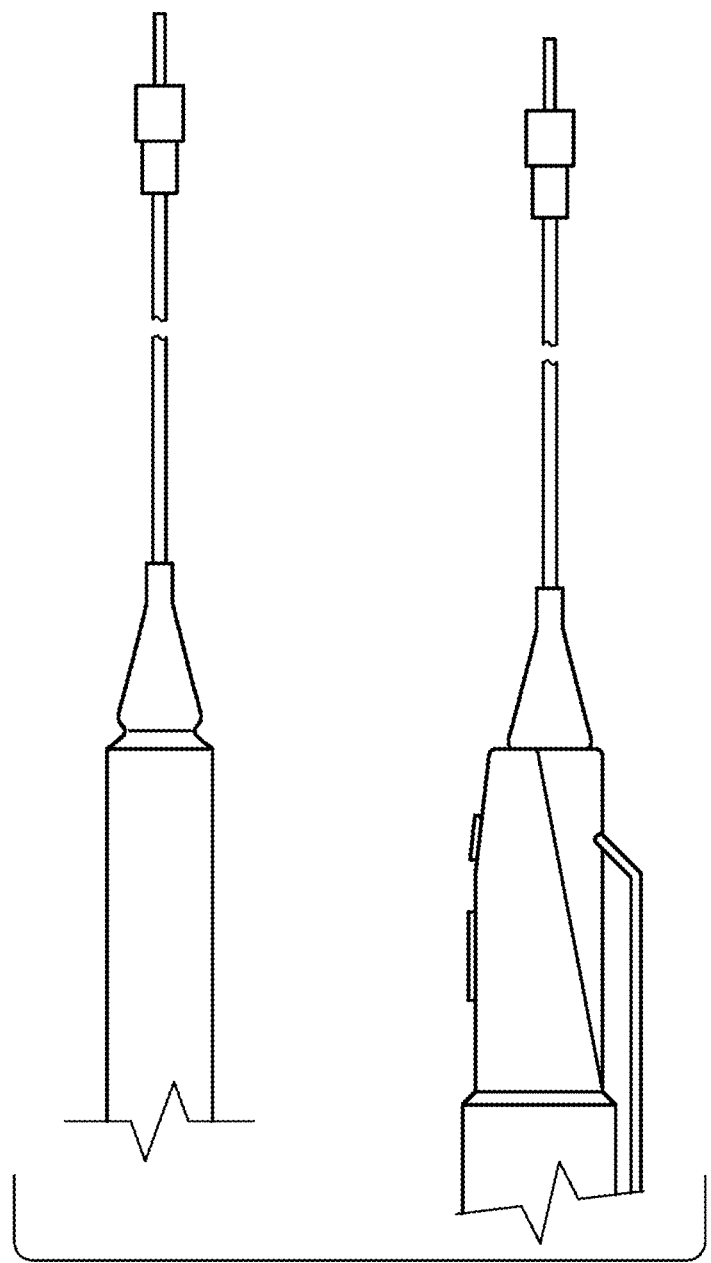
Figure 23:
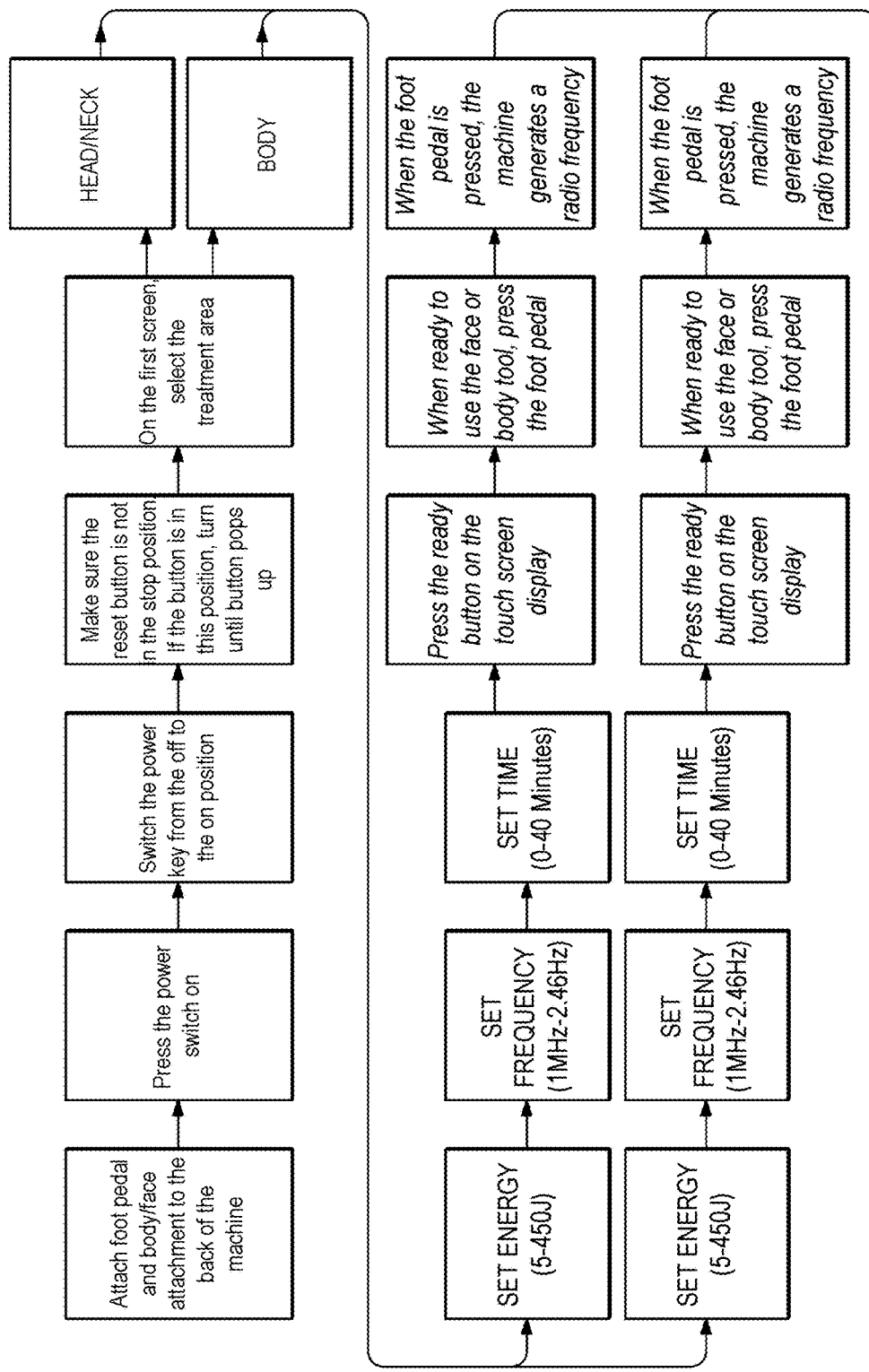
FIG. 23 shows a flow chart of the protocol for using a laser of the present invention.

Referring to FIGS. 22a and 22b, shown is a fiber optic device 400 for use in conjunction with the substrates and methods of the present invention. Fiber optic device 400 is comprised of hand grip assembly 401 disposed between a first end and a second end. The first end is further comprised of nose insert 402 positioned between hand grip assembly 401 and removable nose assembly 404. Bent fiber tube 405 extends from removable nose assembly 405. The second end is further comprised of base insert 406 positioned between hand grip assembly 401 and rubber boot 407. Extending from rubber boot 407 is sheathed fiber 408 having a SMA connector 409 at the end opposite rubber boot 407. FIG. 22c shows a fully assembled fiber optic device 400 further comprising a body for housing the laser source.

Firstly, the conditioner is applied to the root or bone surface. The root conditioner comprises the following at Table 1:

TABLE 1

| Component | |
| --- | --- |
| EDTA | 20-25 g. |
| Calcium gluconate | 10-20 g. |
| Methylparaben | .1-.9 g. |
| Propylparaben | .01-.1 g. |
| Ethanolamine | 2-8 mls. |
| Carboxymethylcellulose | 2-10 g. |
| Green food coloring | 1-2 drops |
| Sterile water | 100 mls. |

The conditioner is optionally rinsed out prior to application of additional substrates or laser light. Alternatively, the conditioner is left on the root or bone surface with the laser light being applied prior to application of any substrate. In an alternative embodiment, the conditioner is left in with only one substrate applied prior to application of the laser light. Optionally, the conditioner is left in the sulcus and substrate is added prior to any application of laser light.

The placement of the substrate into the sulcus containing luminesced blood enables the luminesced blood to coagulate upon the substrate.

Optionally, the liquid substrate or substrate 1 is comprised of the following, per 1 L of solution, at Table 2:

TABLE 2

| Essential Amino Acids | % |
|---|---|
| Isoleucine | 1.125 |
| Leucine | 1.125 |
| Methionine | 1.125 |
| Phenylalanine | 1.125 |
| Threonine | 1.125 |
| Tryptophan | 1.125 |
| Valine | 1.125 |
| Histidine | 1.125 |
| Lysine | 9 |

| Non-Essential Amino Acids | % |
|---|---|
| Alanine | 0.25 |
| Arginine | 0.25 |
| Aspartate | 0.75 |
| Glutamate | 0.25 |
| Glycine | 0.25 |
| Serine | 0.25 |
| Proline | 9 |

| Phosphates | % |
|---|---|
| ADP | 0.667 |
| ATP | 0.667 |
| Acetylcholine | 0.667 |

| Free Bases | % |
|---|---|
| Adenosine | 1.725 |
| Uridine | 1.725 |
| Guanosine | 1.725 |
| Cytidine | 1.725 |
| Benzoic Acid | 1 |
| Sodium Chloride | 1.1 |
| Sterile water | 60 |
| Total: | 100 |

Optionally, the total sterile water component is adjusted 20% up or down, depending on the desired viscosity to be achieved.

In an alternative embodiment, the liquid substrate or substrate 1 is comprised of the following, at Table 3:

TABLE 3

| Essential Amino Acids | Grams |
|---|---|
| Isoleucine | 11.25 |
| Leucine | 11.25 |
| Methionine | 11.25 |
| Phenylalanine | 11.25 |
| Threonine | 11.25 |
| Tryptophan | 11.25 |
| Valine | 11.25 |
| Histidine | 11.25 |
| Lysine | 90 |

| Non-Essential Amino Acids | Grams |
|---|---|
| Alanine | 2.5 |
| Arginine | 2.5 |
| Aspartate | 7.5 |
| Glutamate | 2.5 |
| Glycine | 2.5 |

TABLE 3-continued

| | |
|---|---|
| Serine | 2.5 |
| Proline | 90 |

| Phosphates | Grams |
|---|---|
| ADP | 7-8 |
| ATP | 7-8 |
| Acetylcholine | 6-7 |

| Free Bases | Grams |
|---|---|
| Adenosine | 13-14 |
| Uridine | 13-14 |
| Guanosine | 13-14 |
| Cytidine | 13-14 |
| Iridine | 13-14 |
| Benzoic Acid | 20 |
| Sodium Chloride | .1-.9 |
| Sterile water | .9-1.2 L |

In an alternative embodiment, an additional substrate may be applied, the additional substrate, substrate 2, comprised of: tricalcium phosphate wherein the tricalcium phosphate is precipitated with calcium hydroxide/Claw oil; and hydroxyapatite crystals.

In an alternative embodiment, an additional substrate may be applied, the additional substrate, substrate 3, is comprised of the following at Table 4:

TABLE 4

| Hyaluronic acid | 200 mg to 5.1 g |
|---|---|

| Fatty acids | Grams |
|---|---|
| Linoleic acid (LA) | 4 |
| Alpha-linolenic acid (ALA) | 4 |
| | 8 |

| Sugars (except glucose and fucose) | Grams |
|---|---|
| Mannose | 0.6 |
| Galactose | 0.6 |
| N-acetylgalactosamine | 0.6 |
| N-acetylglucosamine | 0.6 |
| N-acetylneuraminic acid | 0.6 |
| Fucose (L config. and no carboxyl at 6 position) | 0.6 |
| Xylose | 0.6 |
| | 4.2 |
| Glucose | 1.1 |
| Fucose (L config. and no carboxyl at 6 position) | 1.1 |

| Lipids | Grams |
|---|---|
| A | 0.3 |
| D2 | 0.3 |
| D3 | 0.3 |
| E | 0.3 |
| K1 | 0.3 |
| K2 | 0.3 |
| B12 (Methylcobalamin) | 0.3 |
| B12 (Nydroxocobalamin) | 0.3 |
| Cholesterol | 0.3 |
| Diaglycerol | 0.3 |
| | 3.0 |

TABLE 4-continued

| Vitamins | Grams |
|---|---|
| B1 | 0.3 |
| B2 | 0.3 |
| B3 | 0.3 |
| B5 | 0.3 |
| B6 | 0.3 |
| B7 | 0.3 |
| B9 | 0.3 |
| C | 0.3 |
| Pantothenic acid | 0.3 |
| | 2.7 |

| Electrolyte Sources | Grams |
|---|---|
| Calcium chloride | .5 |
| Choline Chloride | .5 |
| Magnesium Sulfate | .5 |
| Potassium Chloride | .5 |
| Potassium Phosphate-monobasic | 1 |
| Sodium Bicarbonate | .5 |
| Sodium Chloride | .5 |
| Sodium Iodide | .5 |
| | 4.5 |

| Metals | Grams |
|---|---|
| Ag nanoparticles | 0.3 |
| Au nanoparticles | 0.3 |
| | 0.6 |

| Iconic metals | Grams |
|---|---|
| Copper | 0.3 |
| Zinc | 0.3 |
| Selenium | 0.3 |
| Iron | 0.3 |
| Manganese | 0.3 |
| Cobalt | 0.3 |
| Chromium | 0.3 |
| Boron | 0.3 |
| Molybdenum | 0.3 |
| | 2.7 |

| Other ionic metals | Grams |
|---|---|
| Boron | 0.3 |
| Silicon | 0.3 |
| Nickel | 0.3 |
| Vanadium | 0.3 |
| | 1.2 |
| Benzoic Acid | Up to 10.1 |
| Sodium Chloride | .1-.9 |
| Sterile water | 60-300 ml |

Optionally, the total sterile water component is adjusted 20% up or down, depending on the desired viscosity to be achieved.

In an alternative embodiment, an additional substrate may be applied, the additional substrate, substrate 4, is comprised of the following at Table 5:

TABLE 5

| Component | Grams | Notes |
|---|---|---|
| carbomer | 10-40 | For acute wound (see FIG. 39) use 10-20<br>For chronic wound (see FIG. 38) use 25-40 |

TABLE 5-continued

| Electrolytes | Grams | |
|---|---|---|
| Potassium chloride | 0.5-3 | |
| Chloride | 0.1-1 | |
| Sodium | 0.1-1 | |
| Potassium | 0.1-1 | |
| Manganese | 0.1-1 | |
| Calcium tri-Phosphate | 0.5-4 | With one size or variety of sizes of crystals: 4-50 μm, 50-150 μm, 100-300 μm, 500-1000 μm, 1-3 mm, and 3-6 mm; may be dense or porous. |
| Sulfate | 0.1-1 | |
| Bicarbonate | 0.1-1 | |
| Snail serum | | 50-150 ml; for chronic wounds substrate 6 may be incorporated (see FIG. 41); decreases depending of volume of substrate 6 |
| Snail secretion filtrate | 50-150 mg | |
| HA | 3-6 | |
| Au | 0.1-1 | |
| Ag | 0.1-1 | |
| Cu | 0.1-1 | |
| Fe | 0.1-1 | |
| Pt | 0.1-1 | |
| Collagen | 50-150 | |
| fucose | 0.5-1 | |
| Glyceine HCl | 0-0.4 | |

Metals may be increased 50% for chronic wounds (see FIG. 40).

Optionally, the total sterile water component is adjusted 20% up or down, depending on the desired viscosity to be achieved.

Substrates 1, 2 and 3 may have different modalities of delivery, for example, drops, sprays, injections or intravenous having the same ingredients, as well as sublingual, anal, foam and ointment formulations or drinkable liquids.

In an alternative embodiment, an additional substrate may be applied, the additional substrate 5 is comprised of the following:

1. collagen, limed and/or
2. collagen, unlimed, and/or
3. collagen, supplemented with porous tricalcium phosphate crystals with one size or variety of sizes: 4-50 μm, 50-150 μm, 100-300 μm, 500-1000 μm, 1-3 mm and 3-6 mm. The tricalcium phosphate crystals may be dense or porous. Optionally, substrate 5 may be used in the absence of other substrates.

In an alternative embodiment, an additional substrate may be applied, the additional substrate 6 is comprised of the following:

1. collagen, limed and/or
2. collagen, unlimed and/or
3. HCl and/or
4. NaCl and/or
5. Cu, Ag, Fe, Au, Pt or any combination thereof and/or
6. Collagen, supplemented with porous tricalcium phosphate crystals with one size or variety of sizes: 4-50 μm, 50-150 μm, 100-300 μm, 500-1000 μm, 1-3 mm and 3-6 mm. The tricalcium phosphate crystals may be dense or porous. Optionally, substrate 6 may be used in the absence of other substrates.

An additional substrate may be applied, the additional substrate comprised of the following: a mixture of tricalcium phosphate and hydroxyapatite crystals. The tricalcium phosphate is precipitated with CaOH/devil's claw oil, in a preferred embodiment. Optionally, the additional substrate includes 50% tricalcium phosphate/devil's claw oil precipitated with 50% porous hydroxyapatite crystals. The tricalcium phosphate crystals used are granules in the following sizes: 4-50 µm, 50-150 µm, 100-300 µm, 500-1000 µm, 1-3 mm and 3-6 mm. The tricalcium phosphate crystals may be dense or porous.

The additional substrate may be comprised of hydroxyapatite crystals of granules containing the following sizes: 10-50 µm, 50-150 µm, 100-300 µm, 500-1000 µm, 1-3 mm and 3-6 mm. The hydroxyapatite crystals may be dense or porous.

In the following examples, the conditioner is applied and subsequently rinsed out. Optionally, the conditioner is left in the sulcus, as the conditioner allowed the micropores within the tooth structures to remain open.

After the conditioner is applied, the sulcus is biostimulated with a laser light. After this occurs, the liquid substrate is applied. Optionally, the additional substrate is applied. For cavities other than oral cavities, a diluted substrate assists treatment when ingested or taken via IV is beneficial although not required.

In an alternative embodiment, an optional spray substrate, spray 1, may be applied, the spray comprised of the following: Au, Ag, Cu, Fe, Pt, and sterile water.

In an alternative embodiment, an optional spray substrate, spray 2, may be applied, the spray comprised of the following: Cl, Na, K, Mg, Phosphate, Sulfate, bicarbonate and sterile water.

The fiber optic device of the present invention is the sole device placed inside the sulcus for treatment. The sulcus may also be treated with laser, RF or laser with RF. The remaining disclosed embodiments of the device may be used in wound treatment in conjunction with the substrates depending on the wound site and severity of the wound. Substrates disclosed herein may be a form including, but not limited to, liquid, tablet, enema, gel, injection or foam.

Alternative RF and/or Laser Assisted Wounded Tissue Regeneration:
1. Scale/root plane;
2. Etch root of tooth;
3. Rinse with saline water;
4. Place tip of laser into the sulcular wound and turn the laser on for 5 seconds;
5. Repeat step 4 circumferentially vertically and horizontally around tooth until the entire sulcular wound has been saturated by laser energy;
6. Place Substrate 1, and/or 2, and/or 3, and/or 4 and/or 5 into glass dappen dishes;
7. Mix the desired amount of substrate 1, and/or 2 and/or 3 and/or 4 and/or 5 in dappen dish;
8. Place the desired mixture into the sulcular wound where bone/tissue loss occurred;
9. Wait a few seconds;
10. Place more of the mixture into the sulcular wound where bone/tissue damage occurred;
11. Wait a few seconds;
12. Repeat steps 8 until all defects have been filled;
13. Wait 1 minute;
14. Place hand piece with its RF tip and/or LED tip, with or without laser, perpendicular to the wound, turn on and keep in position for 1 minute;
15. Wait 10 seconds; and
16. Repeat RF step 14 until entire wound has been covered with RF energy, with or without laser.

Alternative RF and/or Laser Assisted Wounded Tissue Repair:
1. Cleanse wound with saline;
2. Place Substrate 1 and/or 3 onto wound;
3. Direct RF/laser, RF, LED, or laser energy at wound for 1 minute;
4. Place another layer of substrate 1, and/or 2, and/or 3, and/or 4, and/or 5 or any combination thereof onto wound;
5. Wait 10 seconds;
6. Repeat steps 2-5 until wound bed is covered; and
7. Alternatively wait a week in between step 2-6 and gradually cover wound bed.

Treatment of the oral cavity, head/neck, tongue, anal, vaginal region and the deeper areas reached while treating these may be performed with the RF with substrate (applied substrate or drank with water), RF without substrate, RF plus laser with substrate (applied substrate or drank with water), RF plus laser without substrate and laser with substrate (applied substrate or drank with water), laser without substrate. The treatment described may be utilized throughout the gastrointestinal tract, head/neck and anus. The laser, RF or LED treatment applied to the oral cavity and surrounding structures, anal cavity and its surrounding structures, head and neck region and its surrounding structures has benefits in deeper areas of the structures. Those deeper areas of the corresponding structures are thus part of the treatment site. Surrounding structures include, but are not limited to, all bone, cartilage, muscles, tendons, nerves, blood vessels, epithelium and fascia.

RF and/or Laser Assisted Head and Neck Wound Tissue Repair:
1. Drink 4 oz. diluted Substrate 1;
2. Wait 15 minutes;
3. Drink 4 oz. diluted Substrate 3;
4. Wait 15 minutes;
5. Direct RF/laser, RF or laser energy at head and neck location and the surrounding structures where wound occurred;
6. Keep energy in place or move over desired area until desired effect achieved; and
7. Move on to next site until desired result achieved.

Surrounding structures include, but are not limited to, all bone, cartilage, muscles, tendons, nerves, blood vessels, and epithelium.

Head and neck includes, but is not limited to, all structures of the head and neck including esophagus and its surrounding structures, mouth including all interior mouth structures such as tongue (entire area of tongue including but not limited to anterior, posterior, dorsal, ventral, and sublingual), floor of mouth including but not limited to arterial and nerve beds, linea alba, buccal mucosa, buccal flanges, lingual flanges, nose, interior of nose (including but not limited to the epithelial lining), all muscles and other structures of the tongue and surrounding the tongue, all muscles of the eye and surrounding the eye, all arterial, venous and nerve beds of the eye and surrounding the eye. All muscles, nerves, veins, all glands and tissue of the head and neck and any other structure of the head and neck.

RF and/or Laser Assisted Vaginal Wound Repair:
1. Drink 4 oz. diluted Substrate 1;
2. Wait 15 minutes;
3. Drink 4 oz. diluted Substrate 2;
4. Wait 15 minutes;
5. Direct RF/laser, RF or laser energy at the vagina and its surrounding structures;
6. Keep energy in place for 10-20 minutes or until desired effect achieved;
7. Rotate hand piece; and
8. Repeat steps 5-7 until desired result achieved.

Surrounding structures include, but are not limited to, all bone, cartilage, muscles, tendons, nerves, blood vessels, and epithelium.

RF and/or Laser and/or LED Assisted Wound/Tissue Repair—Sphincter Ani Externis:
1. Drink 4 oz. diluted Substrate 1, and/or 2, and/or 3, and/or 4, and/or 5;
2. Wait 15 minutes;
3. Drink 4 oz. diluted Substrate 1, and/or 2, and/or 3, and/or 4, and/or 5;
4. Wait 15 minutes;
5. Direct RF/laser, RF or laser energy at the anus and its surrounding structures;
6. Keep energy in place for 10-20 minutes or until desired effect achieved;
7. Rotate hand piece; and
8. Repeat steps 5-7 until desired result achieved.

Surrounding structures include, but are not limited to, all bone, cartilage, muscles, tendons, nerves, blood vessels, and epithelium and any other structures of the anal cavity.

RF and/or Laser Assisted Wound Repair/Tissue Repair—Breast:
1. Drink 4 oz. diluted Substrate 1, and/or 2, and/or 3, and/or 4, and/or 5;
2. Wait 15 minutes;
3. Drink 4 oz. diluted Substrate 1, and/or 2, and/or 3, and/or 4, and/or 5;
4. Wait 15 minutes;
5. Direct RF/laser, RF or laser energy at the breast and structures related to the breast;
6. Keep energy in place for 10-20 minutes or until desired effect achieved;
7. Rotate hand piece; and
8. Repeat steps 5-7 until desired result achieved.

Related structures include, but are not limited to, all bone, cartilage, muscles, tendons, nerves, blood vessels, lymph nodes and epithelium.

RF and/or Laser Assisted Wound/Tissue Repair, Tongue and its Supporting Structures in the Swallowing Mechanism:
1. Drink 4 oz. diluted Substrate 1, and/or 2, and/or 3, and/or 4, and/or 5;
2. Wait 15 minutes;
3. Drink 4 oz. diluted Substrate 1, and/or 2, and/or 3, and/or 4, and/or 5;
4. Wait 15 minutes;
5. Direct RF/laser, RF or laser energy at tongue and its surrounding structures;
6. Keep energy in place for 10-20 minutes or until desired effect achieved;
7. Rotate hand piece if necessary; and
8. Repeat steps 5-7 until desired result achieved.

Surrounding structures include, but are not limited to, all bone, cartilage, muscles, tendons, nerves, blood vessels, and epithelium.

RF and/or Laser Assisted Wound Regeneration:
1. Drink 4 oz. diluted Substrate 1, and/or 2, and/or 3, and/or 4, and/or 5 and/or 6;
2. Wait 15 minutes;
3. Drink 4 oz. diluted Substrate 1, and/or 2, and/or 3, and/or 4, and/or 5 and/or 6;
4. Wait 15 minutes;
5. Direct RF/laser, RF, LED or laser energy at wound and its surrounding structures;
6. Apply Substrate 1, and/or 2, and/or 3, and/or 4, and/or 5 and/or 6;
7. Direct RF/laser, RF, LED or laser energy wound and its surrounding structures;
8. Keep energy in place for 10-20 minutes or until desired effect achieved;
9. Rotate energy source if necessary; and
10. Repeat steps 5-9 until desired result achieved.
11. Alternatively wait a week in between steps 5-9 and gradually cover wound bed.

Surrounding structures include, but are not limited to, all bone, cartilage, muscles, tendons, nerves, blood vessels, and epithelium.

RF and/or Laser Assisted Pore Repair:
1. Drink 4 oz. diluted Substrate 1, and/or 2, and/or 3, and/or 4, and/or 5;
2. Wait 15 minutes;
3. Drink 4 oz. diluted Substrate 1, and/or 2, and/or 3, and/or 4, and/or 5;
4. Wait 15 minutes;
5. Direct RF/laser, RF or laser energy at pores and their surrounding structures;
6. Keep energy in place for 10-20 minutes or until desired effect achieved;
7. Rotate hand piece; and
8. Repeat steps 5-7 until desired result achieved.

Surrounding structures include, but are not limited to, all bone, cartilage, muscles, tendons, nerves, blood vessels, and epithelium.

RF and/or Laser and/or LED Assisted Oral Cavity Wound Repair:
1. Drink 4 oz. diluted Substrate 1, and/or 2, and/or 3, and/or 4, and/or 5 and/or 6;
2. Wait 15 minutes;
3. Drink 4 oz. diluted Substrate 1, and/or 2, and/or 3, and/or 4, and/or 5 and/or 6;
4. Wait 15 minutes;
5. Direct RF/laser, RF or laser energy at oral cavity and its' surrounding structures;
6. Apply Substrate 1, and/or 2, and/or 3, and/or 4, and/or 5 and/or 6;
7. Direct RF/laser, RF, LED or laser energy wound and its surrounding structures;
8. Keep energy in place for 10-20 minutes or until desired effect achieved;
9. Rotate energy source; and
8. Repeat steps 5-9 until desired result achieved.

Surrounding structures include, but are not limited to, all bone, cartilage, muscles, tendons, nerves, blood vessels, and epithelium.

Further still, wound treatment may be utilized for additional conditions including, but not limited to, vaginal wound repair, breast wound repair/regeneration/generation, anal wound repair, age spot repair, pore repair, skin and tissue repair and general body wound repair.

Figure 33A:
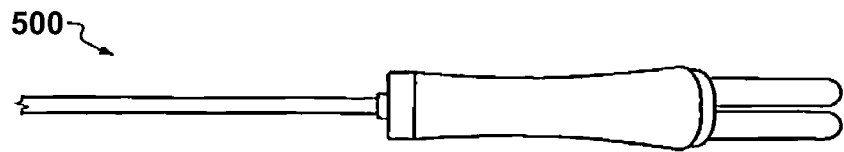
FIG. 33a-33e show various views of an RF hand piece of the present invention. (a) shows a top view. (b) shows a side view. (c) shows a perspective view of the RF tips. (d) shows an exploded side perspective view. (e) shows an alternative side perspective view.
Figure 33B:
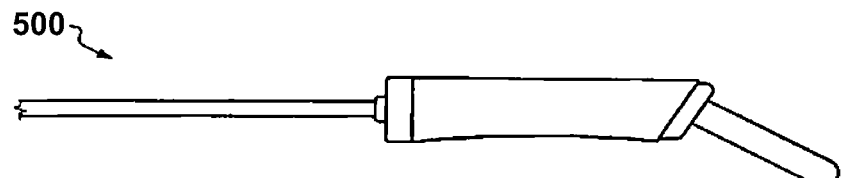
Figure 33C:
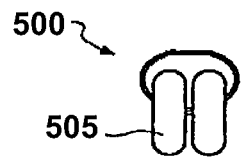
Figure 33D:
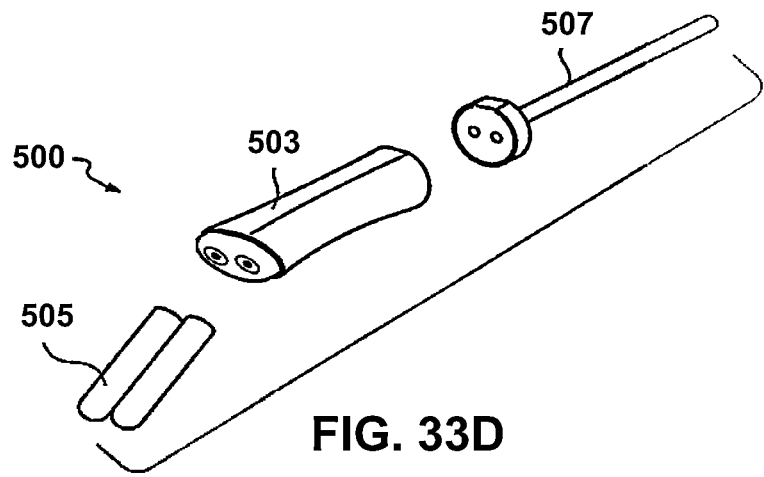
Figure 33E:
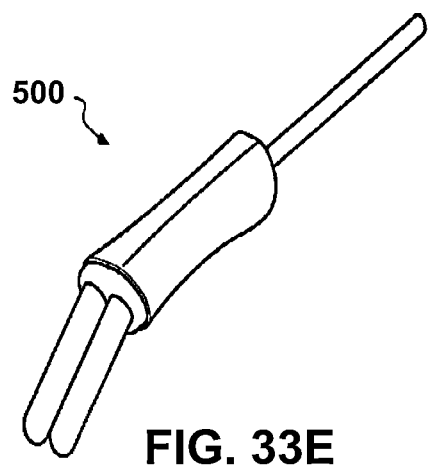

Referring to FIG. 33a-33e, shown is a fourth embodiment of a device 500 for use in conjunction with the substrates and methods of the present invention. FIG. 33a shows a top view of the device 500 of the fourth embodiment. FIG. 33b shows a side view and FIG. 33c shows a close-up of the tip of device 500. Specifically, FIG. 33d illustrates an exploded view of the device 500 comprised of housing 503, tips 505 and energy source 507. Energy source 507 provides RF energy to housing 503 when connected. FIG. 33e shows a side perspective view of the assembled device 500. Optionally, the device 500 may be used in the absence of substrates.

Figure 34C:
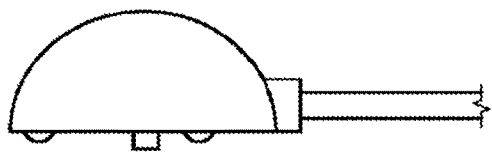
FIG. 34a-34f show various views of a fourth alternative diode laser of the present invention. (a) shows a right side view. (b) shows a front view. (c) shows a left side view. (d) shows a left side perspective view. (e) shows a top view. (f) shows a right side perspective view.
Figure 34F:
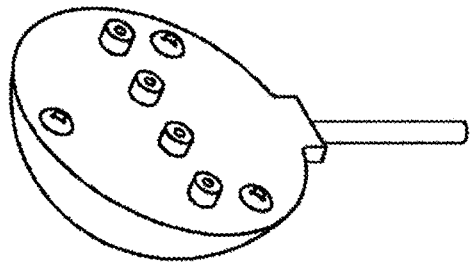
Figure 34B:
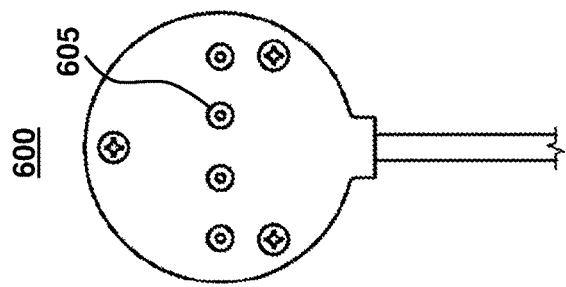
Figure 34E:
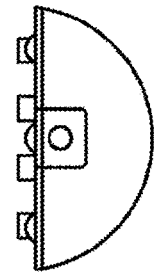
Figure 34A:
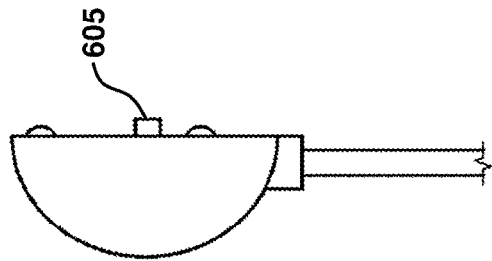
Figure 34D:
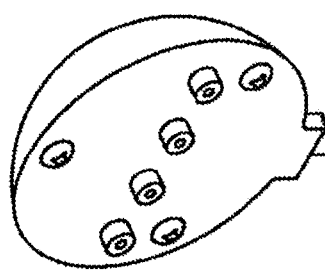

Referring to FIG. 34a-34f, shown is a fifth embodiment of a device 600 for use in conjunction with the substrates and methods of the present invention. FIGS. 34d and 34f show side perspective views of device 600. FIG. 34a shows a side view of device 600 wherein device 600 has a hemispheric shape and is further comprised of a flat surface opposite the hemispheric surface. The flat surface is further comprised of a plurality of mini lasers 605 for delivery of diode laser energy for treatment of an acute wound. The mini lasers 605 are self-contained within device 600. In a preferred embodiment, the laser power used for treatment may be approximately 6-24 mW.

Referring to FIG. 35a-35f, shown is power device 700 for a fiber optic had piece for use in conjunction with the substrates and methods of the present invention. FIG. 35a shows the components of pocket power device 700, the pocket power device 700 further comprised of a base 701, a battery mount 702, a rechargeable battery 703, a handle for a fiber optic laser 704, and a top 705. FIG. 35b-35f show various views of the pocket power device 700. The handle 704 is a self-contained unit having an attached fiber optic line 706 upon which a fiber optic laser head (not shown) is connected. Further, a diode laser module is housed in pocket power device 700.

Figure 36B:
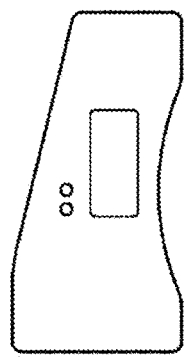
FIG. 36a-36f shows various views of a portable RF transmitter of the present invention. (a) shows a top view. (b) shows a front view. (c) shows a bottom view. (d) shows a left side view. (e) shows a left front perspective view. (f) shows a right front perspective view.
Figure 36D:
Figure 36F:
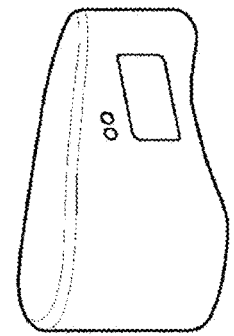
Figure 36A:
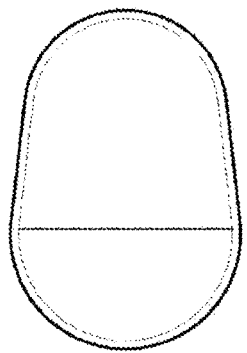
Figure 36C:
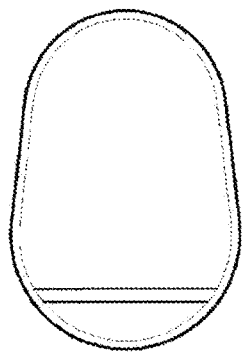
Figure 36E:
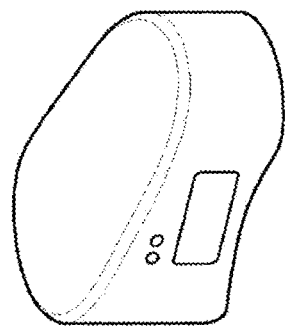

Referring to FIG. 36a-36f, shown is a portable RF transmitter 800 for use in conjunction with the substrates and methods of the present invention. FIGS. 36e and 36f show side perspective views of RF transmitter 800. FIG. 36a shows a top view; FIG. 36b shows front view; FIG. 36c shows a bottom view; and FIG. 36d shows a left side view. Optionally, the RF transmitter 800 may be used in the absence of substrates.

Figure 37A:
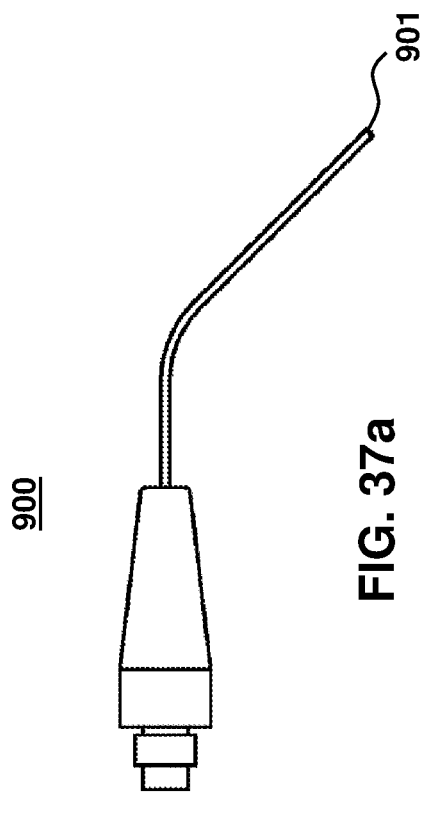
FIG. 37a-37b show alternative fiber optic lasers of the present invention. (a) shows a flat tip. (b) shows a glass dispersion tip.
Figure 37B:
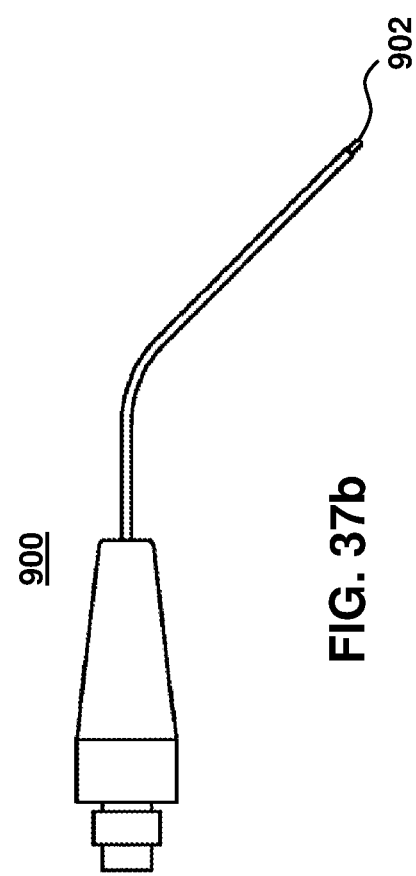

Referring to FIG. 37a-37b, shown are alternative embodiments of interchangeable fiber optic tips for a laser for use in conjunction with the substrates and methods of the present invention. FIG. 37a shows an interchangeable fiber optic tip for a laser having a nose piece 900 and a flat tip 901. FIG. 37b shows an interchangeable fiber optic tip for a laser having a nose piece 900 and a glass dispersion tip 902.

EXAMPLES

I. Analysis of Tooth #15 at 12 Unique Loci

A patient's pocket depths at tooth 15 were measured at 12 separate loci. The root of the tooth was then scaled and planed to remove calculus build up on the root surface. After scaling and planning, bleeding occurs in the sulcus. The sulcus was allowed to air dry and immediately thereafter the conditioner is applied to the sulcus and left for 30 seconds before being rinsed with saline. The tooth was next scaled and planed again to renew blood flow. With blood pooling in the sulcus, the 45° laser tip was placed into the sulcus. The laser light used has a wavelength in the visible portion of the electromagnetic spectrum, between 400 nm-700 nm wavelength. The laser was emitted continuously with only intermittent stops for tissue temperature control. The laser was allowed to penetrate the entire sulcus by moving the tip vertically and horizontally throughout the sulcus for 30 second. The laser tip was cut to 45° in the opposite angle for the second pass into the sulcus and 90° for the third pass to allow the laser bean to penetrate the existing periodontium to decontaminate and biostimulate the sulcular contents.

In the meantime, the first substrate and the second substrate were mixed in a glass dish. Some of the patient's blood that has been treated with the laser light in the sulcus was also mixed in the glass dish. This mixture is then placed immediately into the sulcus upon mixture. Enough of the mixture was placed into the sulcus to fill the sulcus while ensuring the mixture stayed 3 mm below the top of the gingival margin and remained immersed in blood. The patient's mouth was kept open for 5 minutes to ensure the newly formed blood clot containing the substrate mixture remained intact.

Figure 11:
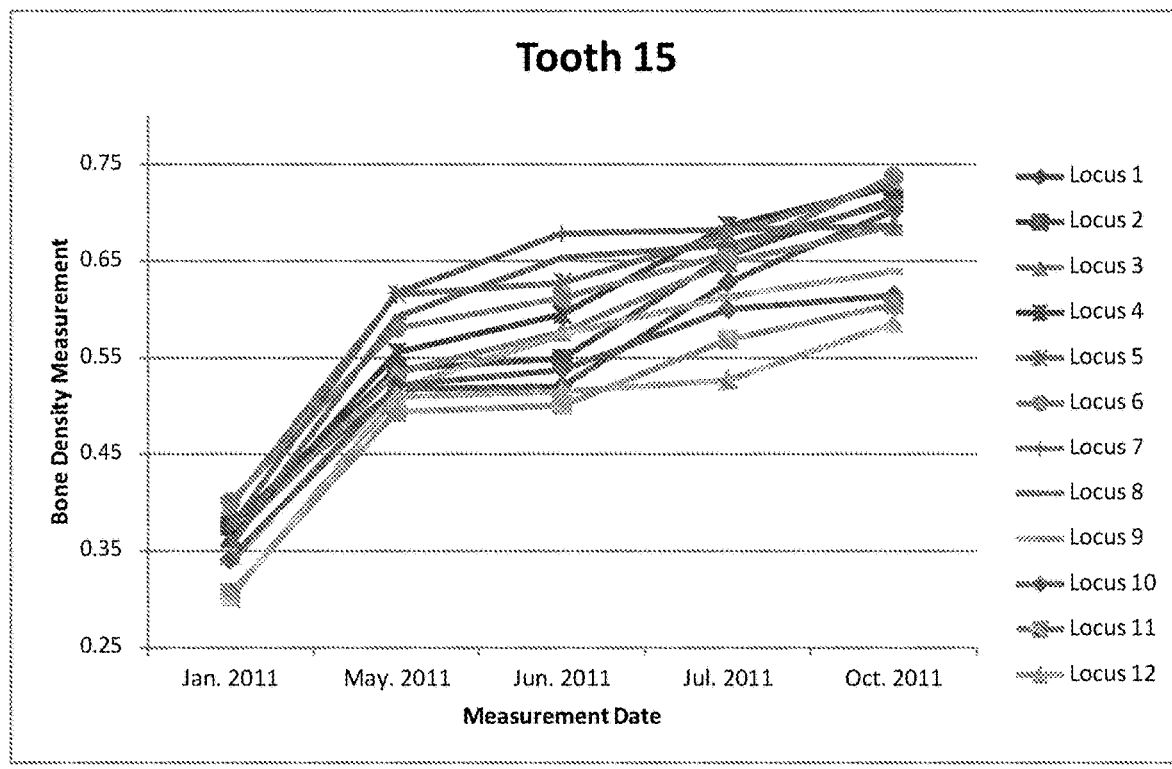
FIG. 11 shows bone density measurements for tooth 15 of a patient at 12 loci on the tooth following treatment with a diode laser and a substrate over time.

Treatment was repeated on tooth 15 on four subsequent occasions, at which time the pocket depths at each loci were measured prior to treatment. Measurements are shown in FIG. 11. The data show an increase in calcium density at the specific loci.

II. Analysis of Tooth #12 at 17 Unique Loci

Figure 12:
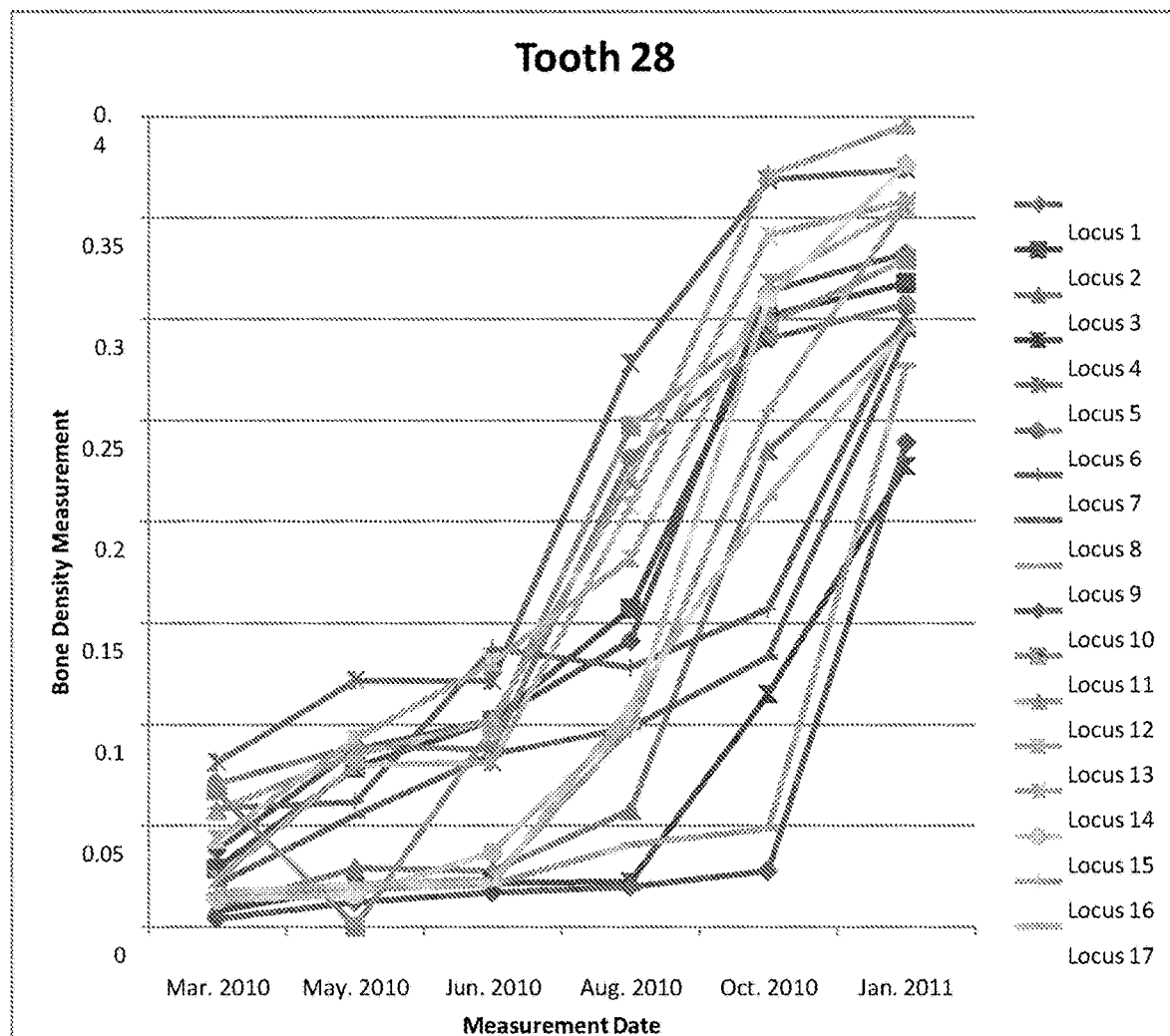
FIG. 12 shows bone density measurements for tooth 28 of a patient at 17 loci on the tooth following treatment with a diode laser and a substrate over time.

A patient's pocket depths at tooth 28 were measured at 17 separate loci. The treatment disclosed herein was performed on five subsequent occasions, at which time the pocket depths at each loci were measured prior to treatment. Measurements are shown in FIG. 12. The data show an increase in calcium density across all loci.

Figure 13:
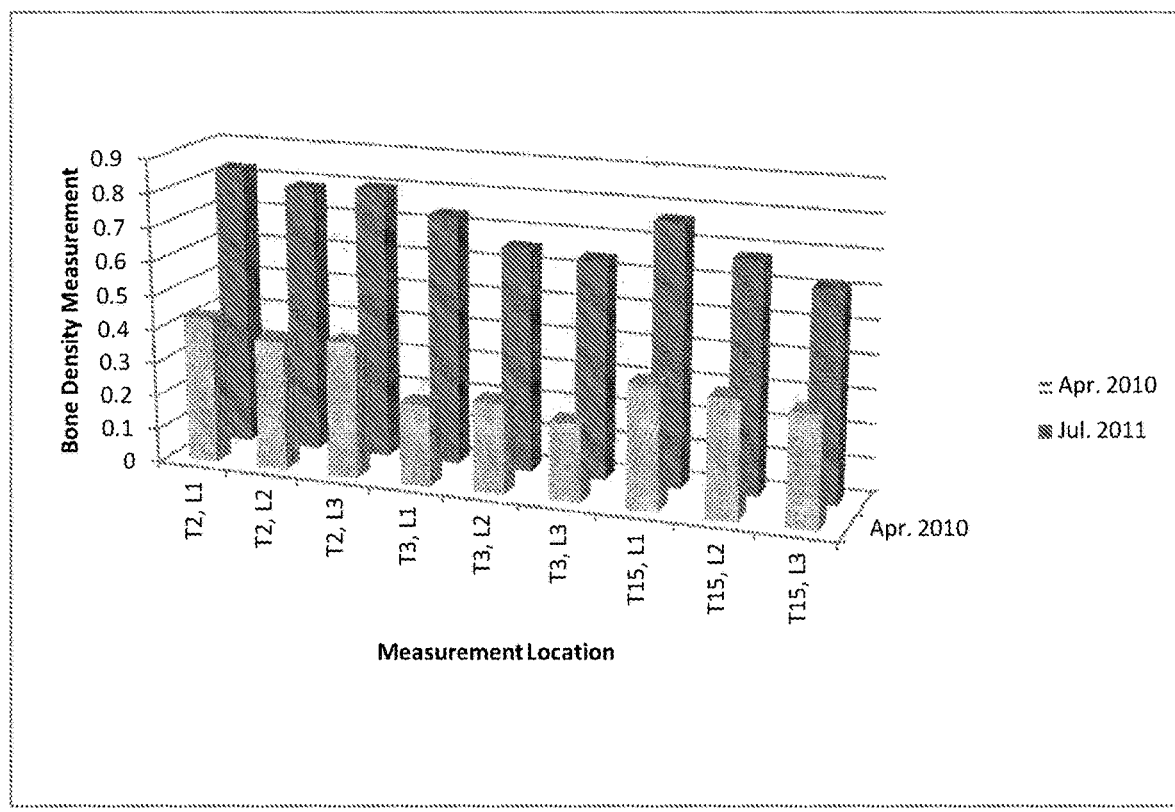
FIG. 13 shows bone density measurements for tooth 2, tooth 3 and tooth 15 of a patient at 3 loci per tooth following treatment with a diode laser and a substrate over time.
Figure 14A:
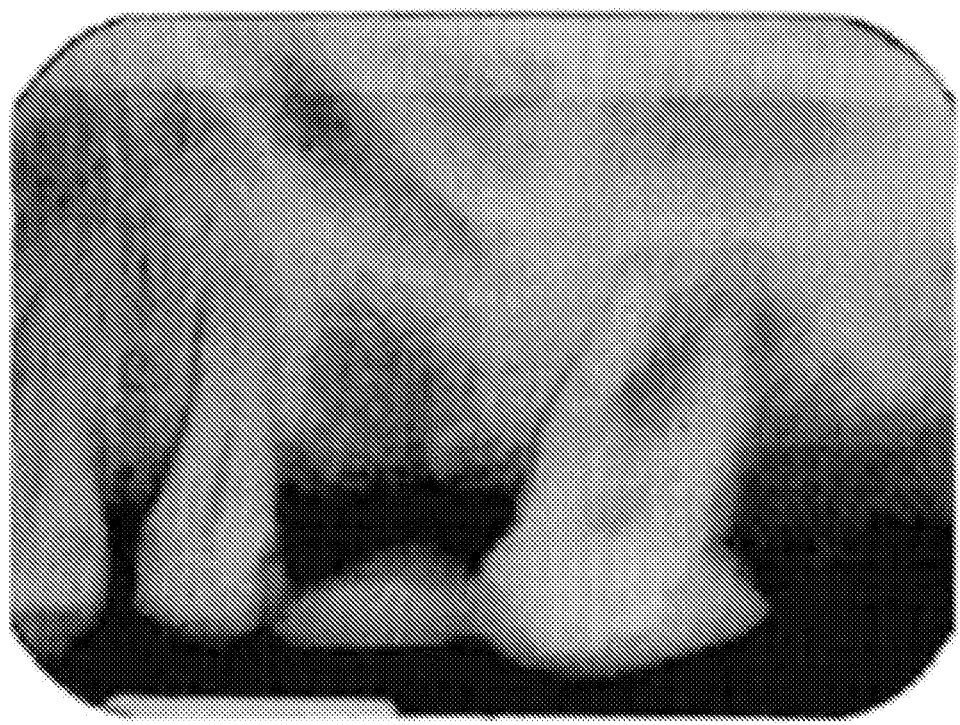
FIGS. 14a and 14b show X-rays of tooth 15 of a patient from which measurements shown in FIG. 11 were collected. (a) shows tooth 15 before treatment. (b) shows tooth 15 at the October 2011 measurement following three treatments.
Figure 14B:
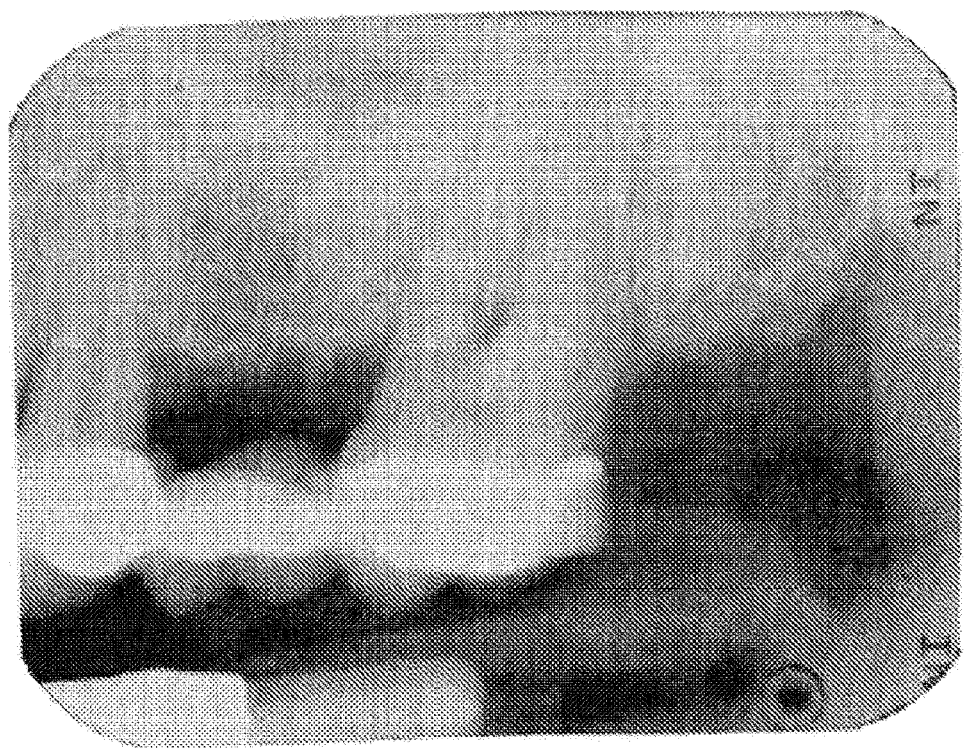
Figure 15A:
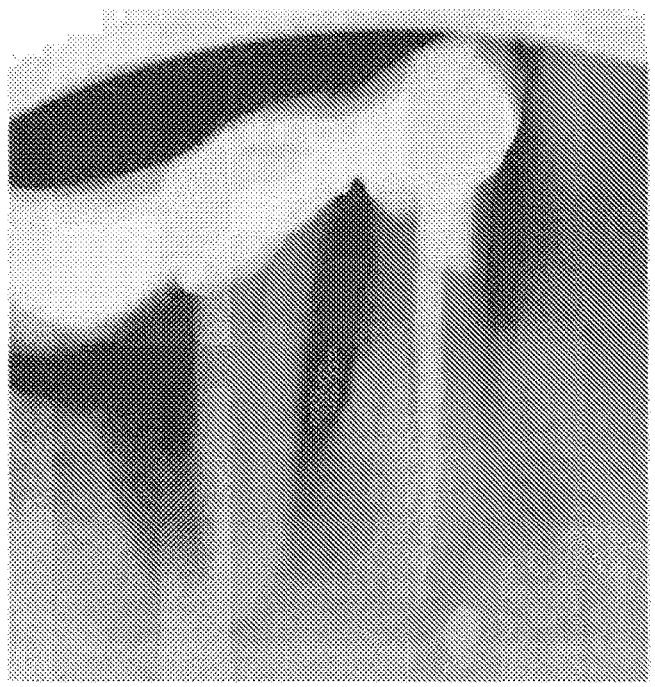
FIGS. 15a and 15b show X-rays of tooth 28 of a patient from which measurements shown in FIG. 12 were collected. (a) shows tooth 28 before treatment. (b) shows tooth 28 at the January 2011 measurement following four treatments.
Figure 15B:
Figure 16A:
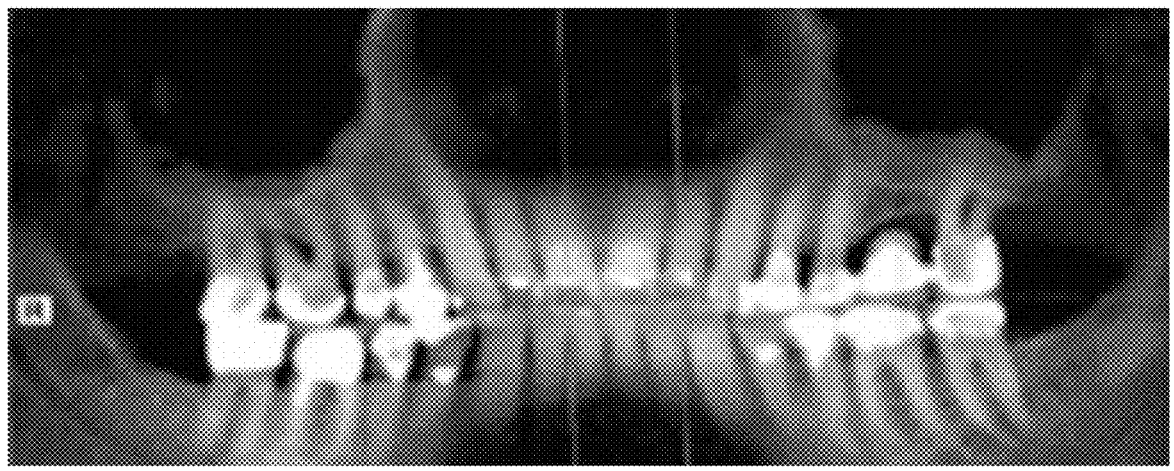
FIGS. 16a and 16b show a panoramic X-ray of tooth 2, tooth 3 and tooth 15 of a patient from which measurements shown in FIG. 13 were collected. (a) shows the teeth before treatment. (b) shows the teeth at the July 2011 measurement.
Figure 16B:
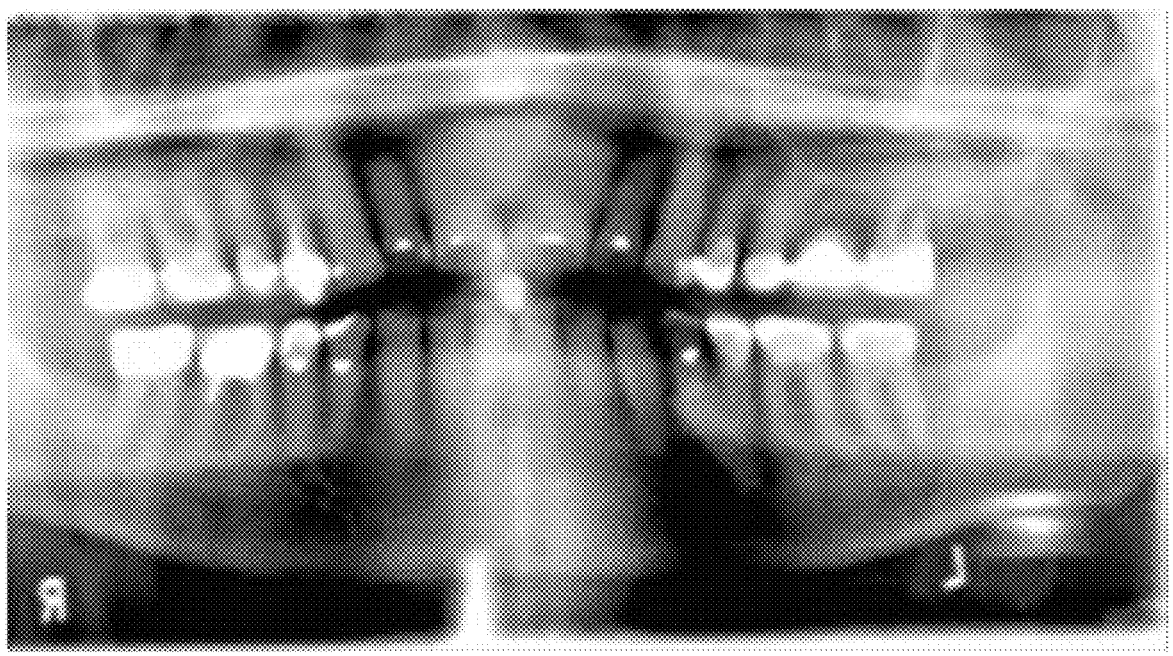

III. Analysis of Tooth #2, #3 and #15 at 3 Unique Loci Per Tooth A patient's pocket depths at tooth 2, tooth 3 and tooth 15 were measured at three separate loci per tooth. The treatment disclosed herein was performed 3 months after the initial treatment, at which time the pocket depths at each loci were measured prior to treatment. Measurements are shown in FIG. 13. The data show a progression of bone generation.

IV. Analysis of Chin Profile

Figure 24:
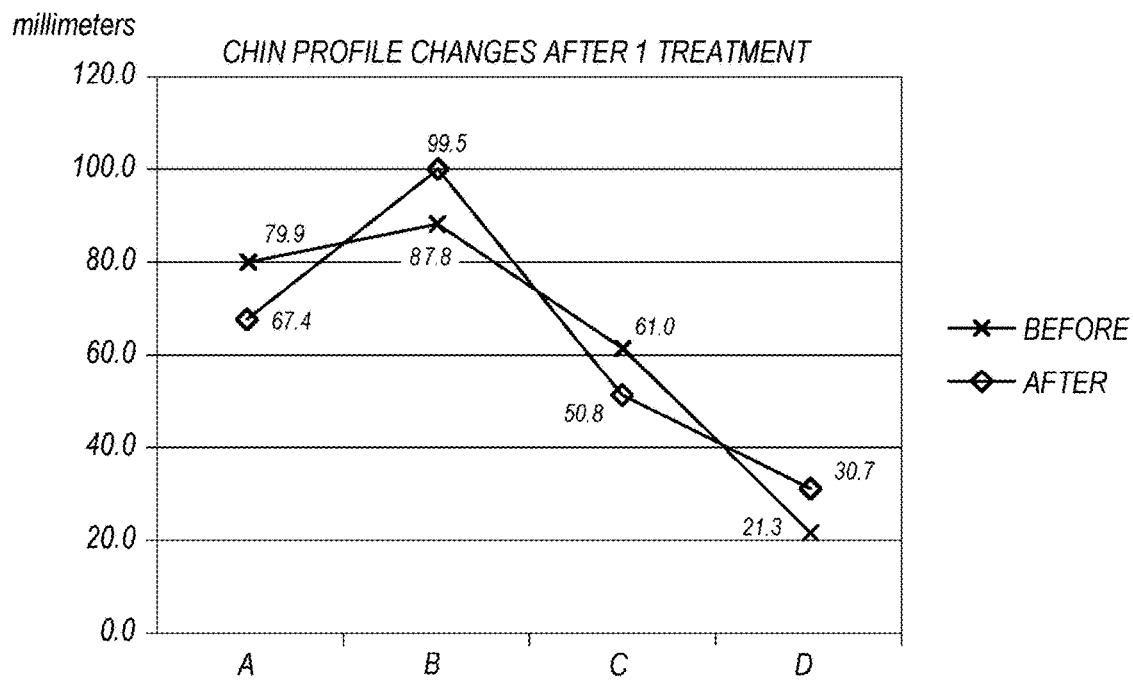
FIG. 24 shows chin profile measurements before and after treatment.

A patient's chin profile was measured. The treatment disclosed herein was performed once after the initial measurements were taken with measurements repeated following treatment. Measurements are shown in FIG. 24. The data show a general increase in chin profile following a single treatment.

V. Analysis of Toe Crease

Figure 25:
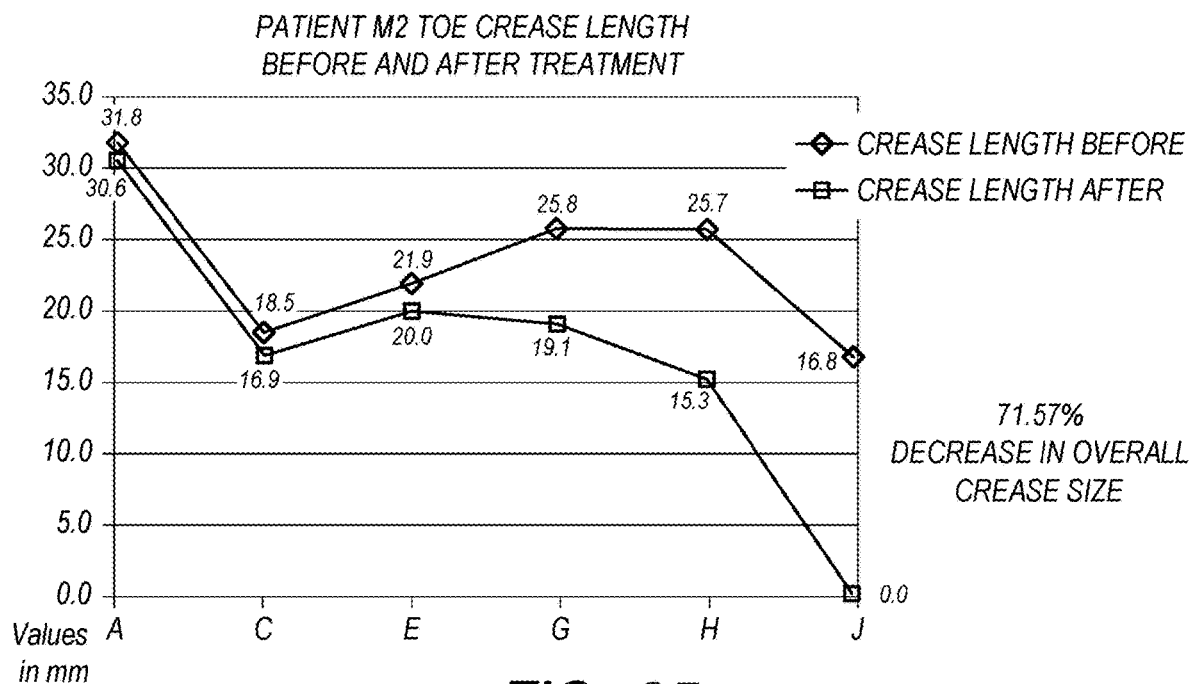
FIG. 25 shows toe crease length measurements before and after treatment.

A patient's toe crease length was measured. The treatment disclosed herein was performed after initial measurements were obtained with measurements repeated following treatment. Measurements are shown in FIG. 25. The data show a 71% overall decrease in crease size following treatment.

VI. Analysis of Gingival Wound Tissue

A patient's gingival wounds were measured from the line to the top of the gingiva. The treatment disclosed herein was performed and measurements were repeated following treatment. Images of gingival wounds are shown before and after treatment in FIGS. 26a and 26b. Measurements are shown in FIG. 26c. The data show a 50% or greater decrease in the wound following a single treatment.

VII. Analysis of Hand Crease

Figure 27:
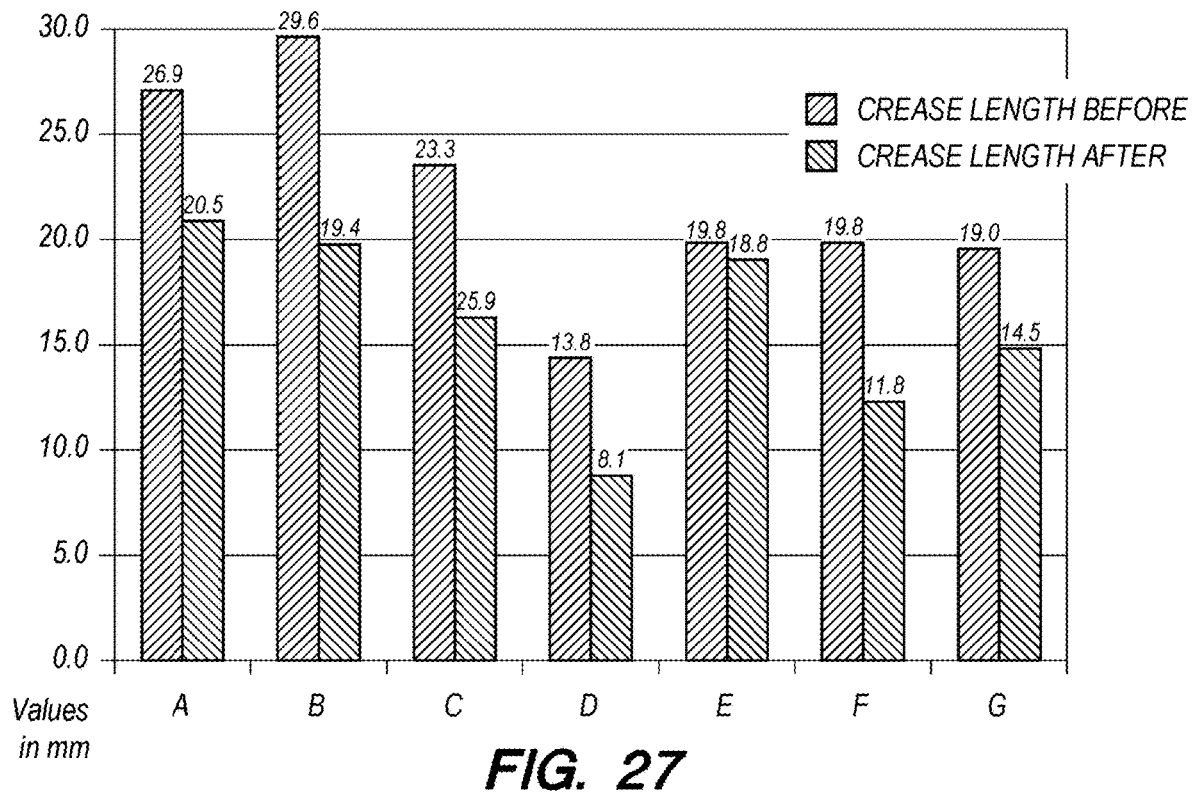
FIG. 27 shows hand crease length measurements before and after treatment.

A patient's hand crease length was measured. The treatment disclosed herein was performed after initial measurements were taken with measurements repeated following treatment. Measurements are shown in FIG. 27. The data show an overall decrease in crease length following treatment.

VIII. Analysis of New Skin Growth

Figure 28:
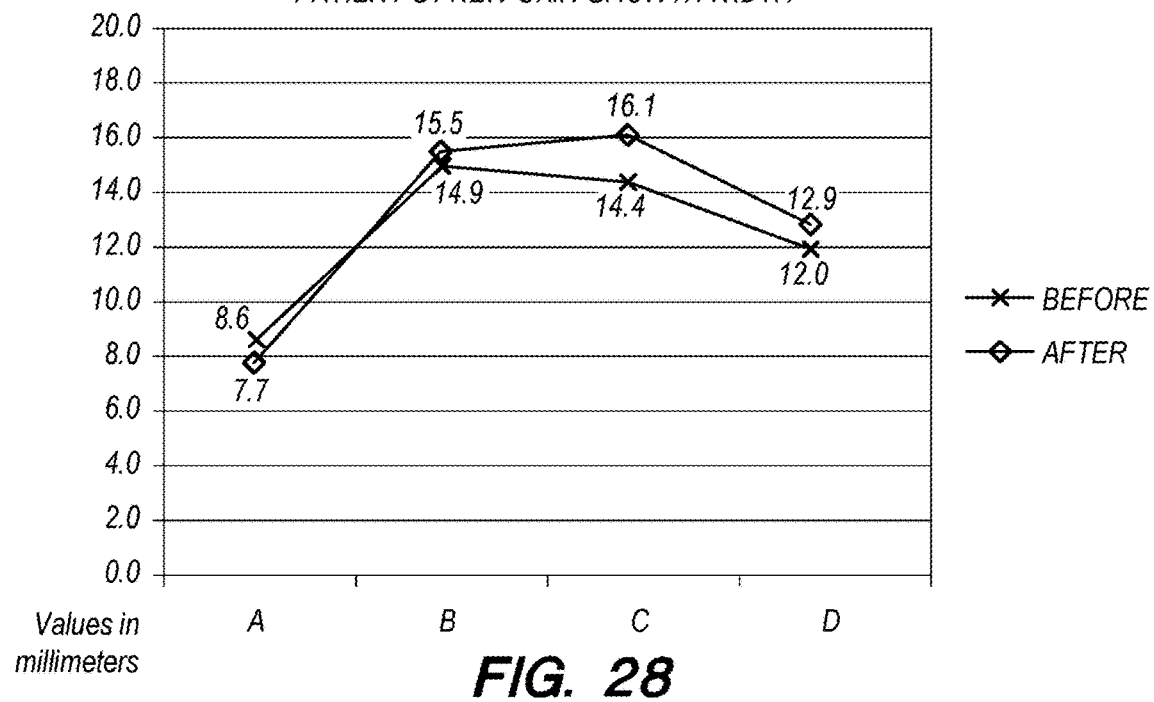
FIG. 28 shows wound new skin growth measurements before and after treatment.

A patient's skin leg wound was measured. The treatment disclosed herein was performed after initial measurements were taken with measurements repeated following treatment. Measurements are shown in FIG. 28. The data show an overall increase in new skin growth following treatment. In a preferred embodiment, chronic wounds on limbs may be treated using a three-sided LED system wherein the treatment unit is placed around the limb on three sides and applies the LED energy to a larger surface area. The LED system uses an energy source no greater than 60 mW.

IX. Analysis of Anal Scar Reduction

Figure 29:
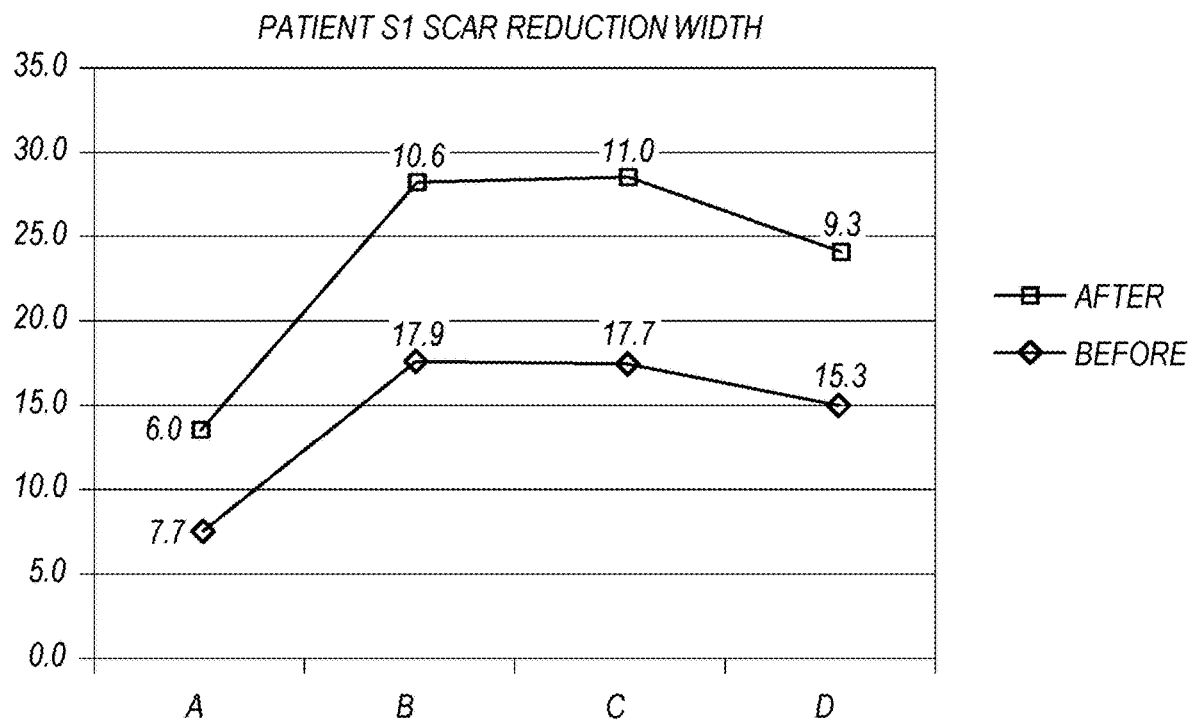
FIG. 29 shows (anal) scar width reduction measurements before and after treatment.
Figure 30:
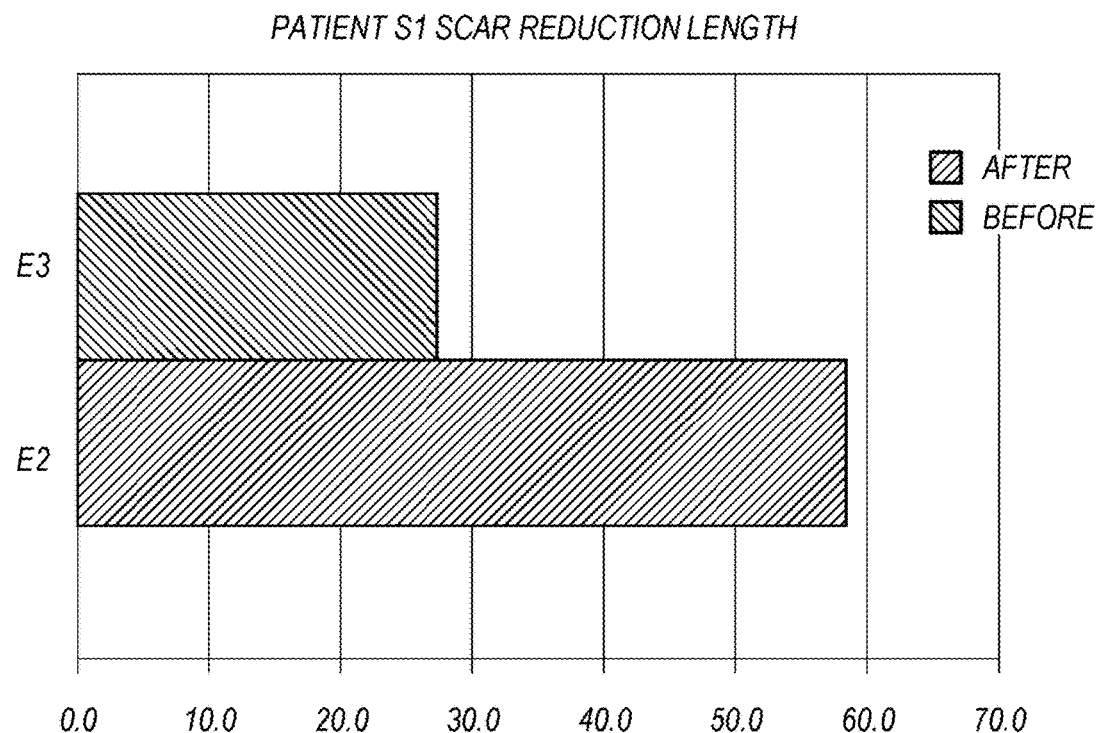
FIG. 30 shows (anal) scar length reduction measurements before and after treatment.

A patient's anal scar tissue was measured. The treatment disclosed herein was performed after initial measurements were taken with measurements repeated following treatment. Measurements are shown in FIG. 29 and FIG. 30. The data show a reduction in both length and width of scar tissue following treatment.

X. Analysis of Tongue Strength

Figure 31:
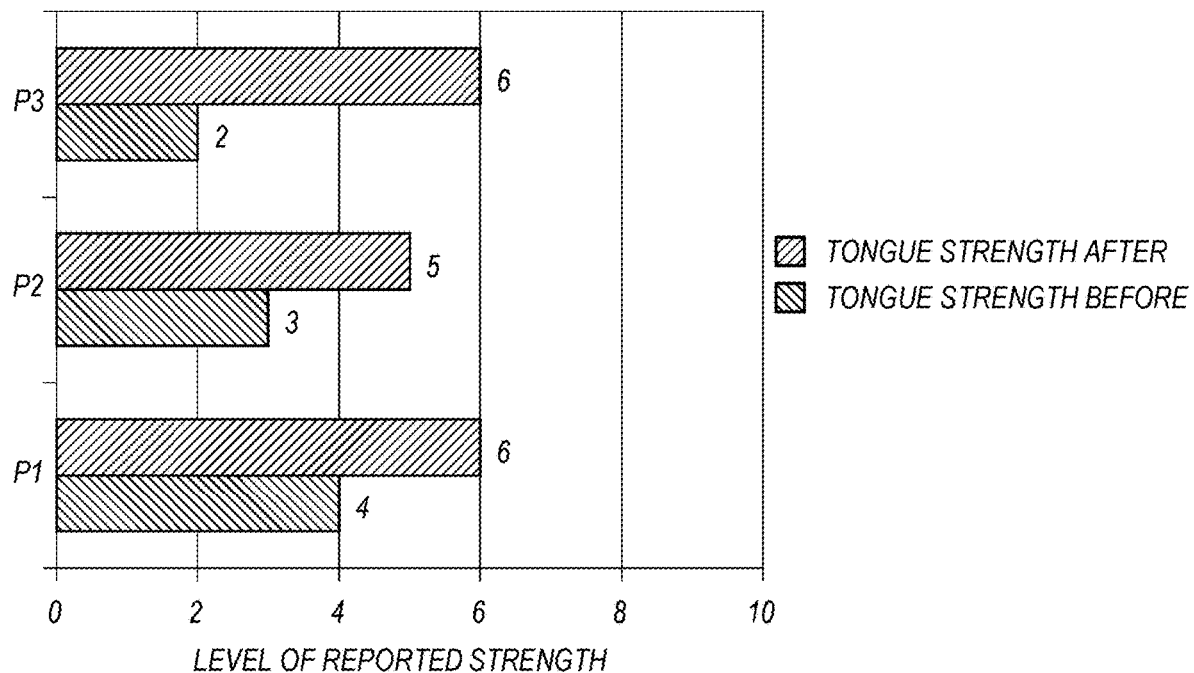
FIG. 31 shows swallowing strength measurements before and after treatment.

Tongue strength and swallowing was assessed for three patients. The treatment disclosed herein was performed after initial assessments were made and tongue strength and swallowing were reevaluated following treatment. Measurements are shown in FIG. 31. The data show each patient experiencing an increase in tongue strength following treatment.

XI. Analysis of Breast Firmness

Figure 32:
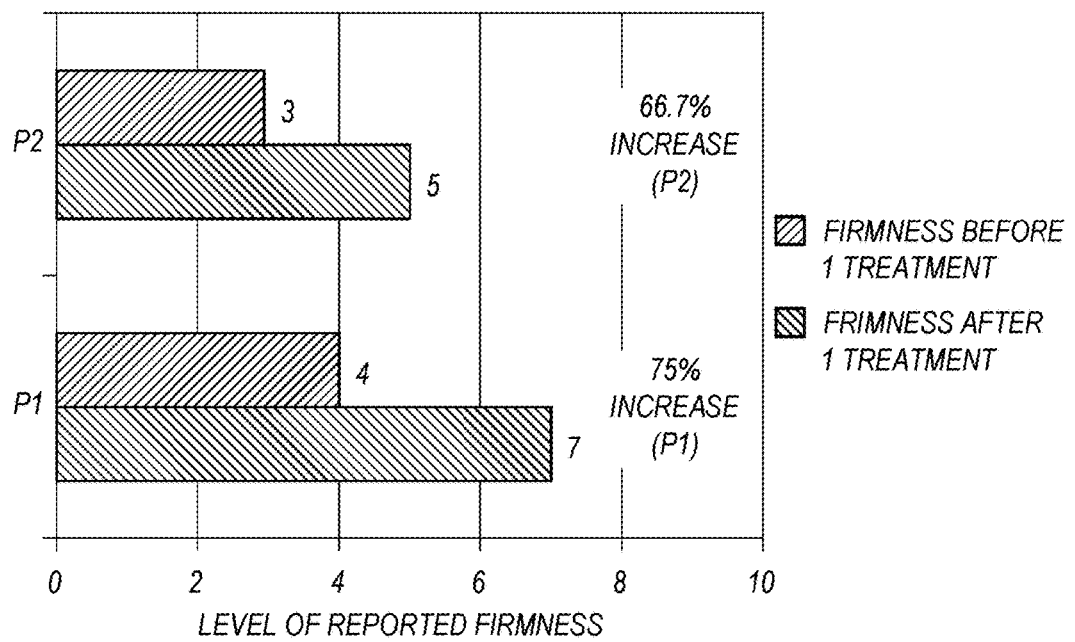
FIG. 32 shows breast firmness measurements before and after treatment.

Breast firmness was recorded for two patients. The treatment disclosed herein was performed after initial assessments were made and breast firmness was reevaluated following treatment. Comparative firmness is shown in FIG. 32. The data show the patients experiencing an increase in firmness of 75% and 66.7% following treatment, respectively.

XII. Analysis of Epithelial Wound Regeneration

Figure 38:
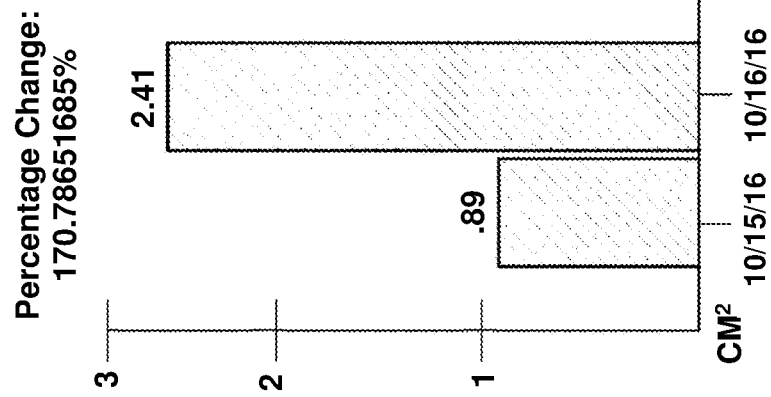
FIG. 38 shows epithelial wound regeneration before and after treatment.

The epithelial wound regeneration of a patient was assessed. The treatment disclosed herein was performed after initial wound measurement and wound size was remeasured following treatment. Comparative measurements are shown in FIG. 38. Epithelial regeneration was found to have increased in area by 170% one day following treatment.

XIII. Analysis of Calcaneal Tendon Wound Regeneration

Figure 39:
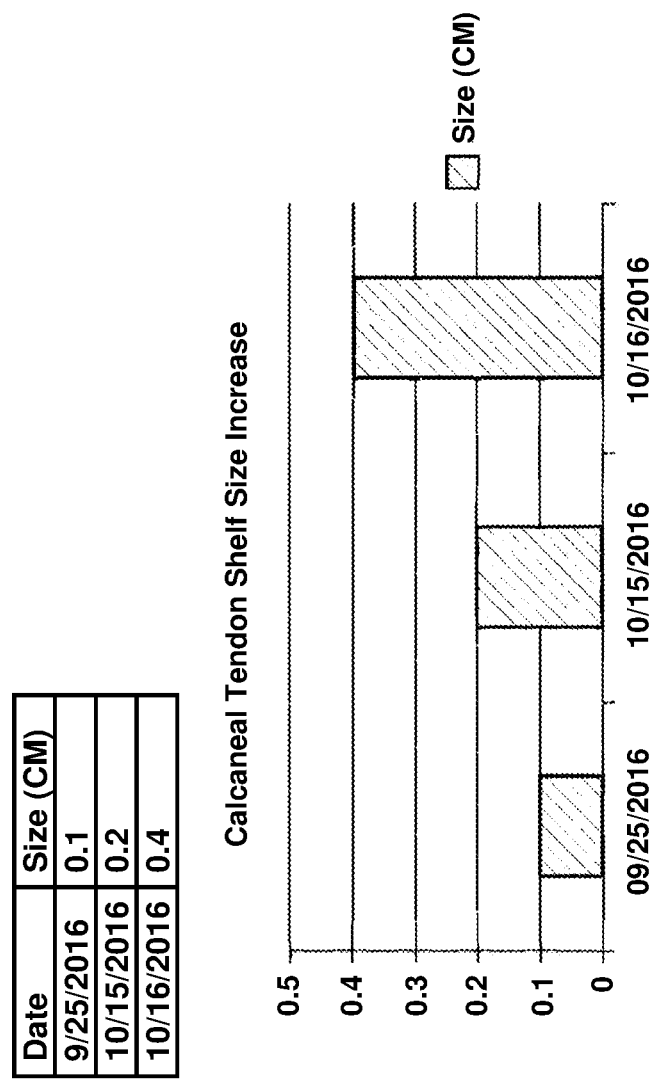
FIG. 39 shows cancaeal tendon wound regeneration before and after treatment.

The calcaneal tendon wound regeneration of a patient was assessed. The treatment disclosed herein was performed after initial wound measurement and wound size was remeasured following treatment. Comparative measurements are shown in FIG. 39. Tendon shelf size increased four times from the initial measurement to the third and final measurement.

XIII. Analysis of Ankle Epithelial Wound Regeneration

The ankle epithelial wound regeneration of a patient was assessed. The treatment disclosed herein was performed after initial wound measurement and wound size was remeasured following treatment. Comparative measurements for two treatment areas are shown in FIG. 40. Epithelial regeneration was found to have increased in area by 264% five months following treatment.

XIV. Analysis of Ankle Wound Size Reduction

The ankle epithelial wound size reduction of a patient was assessed. The treatment disclosed herein was performed after initial wound measurement and wound size was remeasured following treatment. Comparative measurements for two treatment areas are shown in FIG. 41. Epithelial wound size was found to have decreased in area by 72% five months following treatment.

XV. Analysis of Oral Cavity Wound Regeneration

Figure 42:
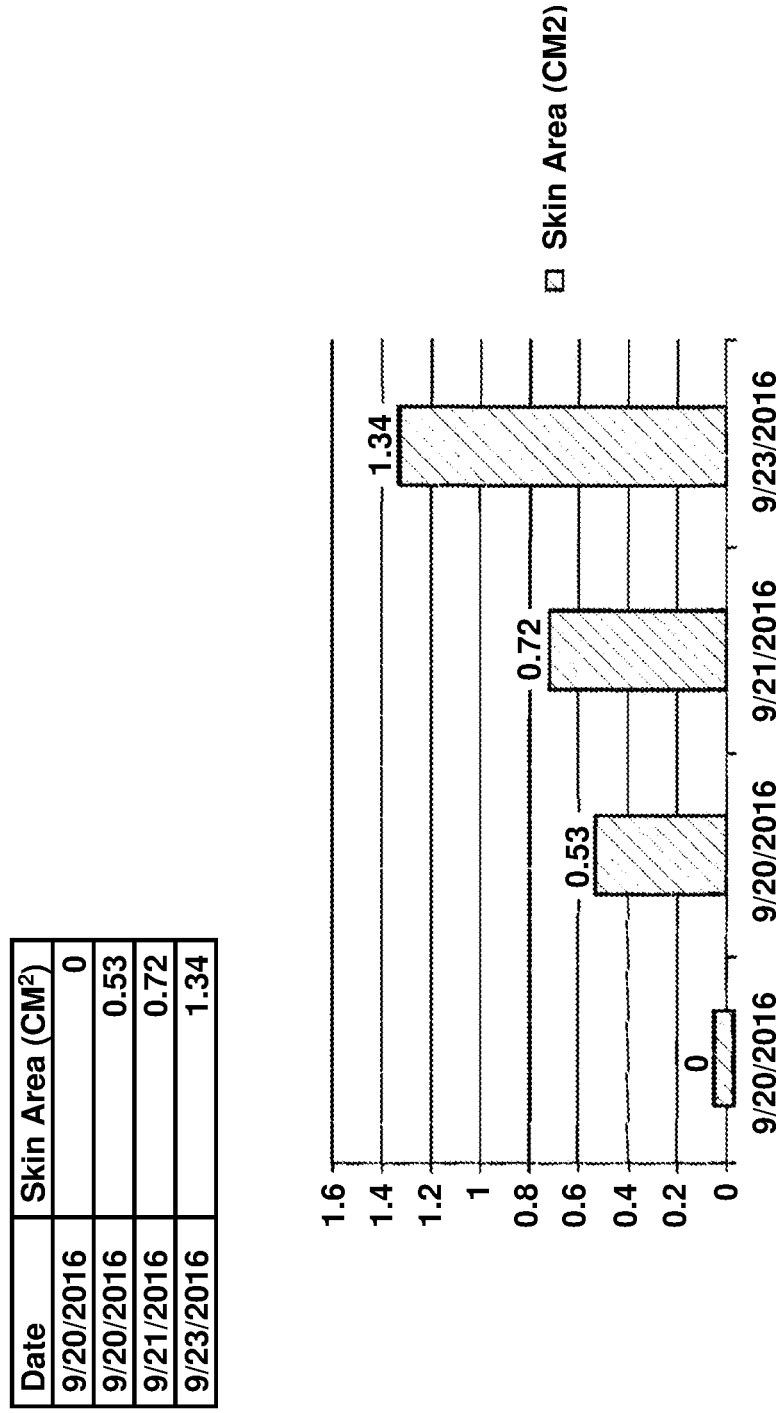
FIG. 42 shows oral cavity wound regeneration before and after treatment.

The oral cavity epithelial wound regeneration of a patient was assessed. The treatment disclosed herein was performed after initial wound measurement and wound size was remeasured following treatment. Comparative measurements are shown in FIG. 42. Epithelial regeneration size increased by 1.34 $cm^2$ from the initial measurement to the fourth and final measurement.

XVI. Analysis of Vein Wound Regeneration

Figure 43A:
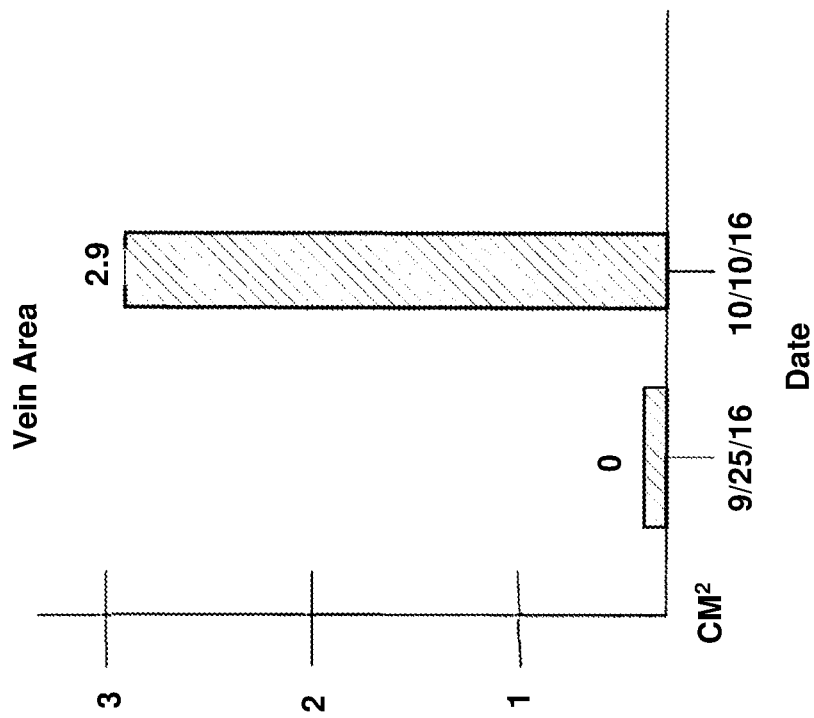
FIG. 43a-b shows (a) vein wound regeneration before and after treatment and (b) a flashlight style infrared laser.
Figure 43B:
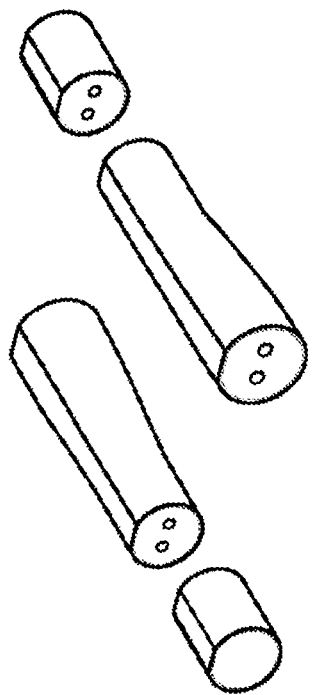

The vein wound regeneration of a patient was assessed. The treatment disclosed herein was performed after initial wound measurement and wound size was remeasured following treatment. Comparative measurements are shown in FIG. 43a. Epithelial regeneration size increased by 2.9 $cm^2$ from the initial measurement to final measurement. Treatment was conducted using a flashlight style infrared laser as shown in FIG. 43b wherein the LED beam is a concentrated flat line of light applied to the skin and veins. The flashlight style laser is a self-contained modular laser that allows for manipulation of skin around a wound during treatment. Alternatively, a LED panel may be used.

One embodiment of the present invention provides a device for treating a wound according to the method described herein, the device emitting a laser a beam of light having a wavelength in the green wavelength range (520-570 nm), red wavelength range (620-750 nm), or yellow wavelength range (570-590 nm) having an alternative wattage of 0.001 W to 5 W, preferably 0.002 W to 4 W, more preferably 0.003 W to 3 W, and most preferably 0.005 W to 2 W. Optionally, the laser light utilizes the IR wavelength range (700 nm-1400 nm) at a laser power of 0.001 W to 5 W to treat wounds. Optionally, a LED light utilizes the IR wavelength range to treat wounds.

Another embodiment of the present invention provides a device for treating a wound according to the method described herein, the device emitting a RF beam up to 10 W comprised of a carrier wave frequency in the range of 0.1 MHz to 20 MHz and a non-sinusoidal waveform in the range of 0 to 40 KHz. In a preferred embodiment, the carrier wave frequency is in the range of 0.2 MHz to 10 MHz, preferably 0.3 MHz to 5 MHz. Optionally a 0.001 W to 10 W range RF energy, preferably a 0.001 W to 3 W range, is utilized in the hertz range of 40 Hz to 24 GHz. In a further alternative embodiment, the RF wave is more than one sine wave wherein the more than one demonstrates a harmonics pattern. Optionally, the non-sinusoidal waveform may be in the range of the above parameters in the absence of a carrier wave.

Yet another embodiment of the present invention provides a device for treatment of a wound according to the method described herein, the device emitting a laser beam, a RF beam or a combination thereof.

Still another embodiment of the present invention provides a device for treatment of wounds in the oral cavity according to the method described herein, the device emitting a fiber optic laser beam. In a preferred embodiment, the fiber optic device may be used in conjunction with the laser and RF device for treating general wounds and wounds of the oral cavity. Optionally, the device emits a LED light.

While there have been shown and described and pointed out the fundamental novel features of the invention as applied to the preferred embodiments, it will be understood that the foregoing is considered as illustrative only of the principles of the invention and not intended to be exhaustive or to limit the invention to the precise forms disclosed.

Obvious modifications or variations are possible considering the above teachings. The embodiments discussed were chosen and described to provide the best illustration of the principles of the invention and its practical application to enable one of ordinary skill in the art to utilize the invention in various embodiments and with various modifications as are suited to the particular use contemplated All such modifications and variations are within the scope of the invention as determined by the appended claims when interpreted in accordance with the breadth to which they are entitled.

What is claimed is:

1. An aqueous or gel substrate for treating damage to a tissue in a form of an acute or chronic wound, comprising:
   (1) collagen,
   (2) 200 mg-6 g of hyaluronic acid,
   (3) water,
   (4) 0.1 g -1 g of Cu,
   (5) 0.1 g -1 g of Fe, and
   (6) 0.1 g -1 g of silver.

2. The substrate of claim 1, wherein the collagen comprises collagen limed, collagen unlimed, or collagen supplemented with porous tricalcium phosphate crystals.

3. The substrate of claim 1, wherein the silver is soluble.

4. The substrate of claim 1, further comprising HCl.

5. The substrate of claim 1, further comprising a phosphate comprising ATP.

6. The substrate of claim 1, further comprising non-native or xenograft hyaluronic acid, and non-native or xenograft collagen limed or unlimed, the non-native or xenograft hyaluronic acid and non-native or xenograft collagen limed or unlimed not being found at or near the wound or any other damaged tissue.

7. The substrate of claim 1, wherein the acute or chronic wound is located on an epithelial surface of the tissue.

8. The substrate of claim 1, wherein the substrate further comprises an effective amount of tricalcium phosphate or dense or porous hydroxyapatite in a variety of crystal sizes.

9. The substrate of claim 1, wherein the substrate comprises silver nanoparticles.

10. A method for treating damage to a tissue in a form of an acute or chronic wound, comprising:
   placing an aqueous or gel substrate into the wound, the substrate comprising:
   (1) collagen,
   (2) 200 mg-6 g of hyaluronic acid,
   (3) water,
   (4) 0.1 g -1 g of Cu,
   (5) 0.1 g -1 g of Fe, and
   (6) 0.1 g -1 g of silver; and
   causing tissue regeneration in the wound with the substrate, wherein the tissue regeneration facilitates healing of the wound.

11. The method of claim 10, further comprising maintaining the substrate in the wound for a period of time, wherein a combination of the (1) collagen, (2) hyaluronic acid, (3) water, (4) Cu, (5) Fe, and (6) silver, is configured to cause the tissue regeneration in the wound and facilitate the healing of the wound.

12. The method of claim 10, wherein the collagen comprises collagen limed, collagen unlimed, or collagen supplemented with porous tricalcium phosphate crystals.

13. The method of claim 10, wherein the silver is soluble.

14. The method of claim 10, the substrate further comprising HCl.

15. The method of claim 10, the substrate further comprising a phosphate comprising ATP.

16. The method of claim 10, the substrate further comprising non-native or xenograft hyaluronic acid, and non-native or xenograft collagen limed or unlimed, the non-native or xenograft hyaluronic acid and non-native or xenograft collagen limed or unlimed not being found at or near the wound or any other damaged tissue.

17. The method of claim 10, wherein the substrate further comprises an effective amount of tricalcium phosphate or dense or porous hydroxyapatite in a variety of crystal sizes.

18. The method of claim 10, wherein the substrate comprises silver nanoparticles.

\* \* \* \* \*